United States Patent
Yersin et al.

(10) Patent No.: US 11,201,291 B2
(45) Date of Patent: Dec. 14, 2021

(54) ORGANIC MOLECULES HAVING TWO NON-CONJUGATED BRIDGES BETWEEN A DONOR AND AN ACCEPTOR FOR EFFECTIVE THERMALLY ACTIVATED DELAYED FLUORESCENCE FOR USE IN OPTOELECTRONIC DEVICES

(71) Applicant: SICHUAN KNOWLEDGE EXPRESS INSTITUTE FOR INNOVATIVE TECHNOLOGIES CO., LTD, Sichan (CN)

(72) Inventors: Hartmut Yersin, Sinzing (DE); Rafal Czerwieniec, Obertraubling (DE); Larisa Mataranga-Popa, Regensburg (DE)

(73) Assignee: SICHUAN KNOWLEDGE EXPRESS INSTITUTE FOR INNOVATIVE TECHNOLOGIES CO., LTD, Sichan (CN)

( * ) Notice: Subject to any disclaimer, the term of this patent is extended or adjusted under 35 U.S.C. 154(b) by 234 days.

(21) Appl. No.: 15/748,509

(22) PCT Filed: Jul. 28, 2016

(86) PCT No.: PCT/EP2016/068037
§ 371 (c)(1),
(2) Date: Jan. 29, 2018

(87) PCT Pub. No.: WO2017/017205
PCT Pub. Date: Feb. 2, 2017

(65) Prior Publication Data
US 2018/0219159 A1    Aug. 2, 2018

(30) Foreign Application Priority Data

Jul. 30, 2015 (DE) ..................... 10 2015 112 501.3
Apr. 4, 2016 (DE) ..................... 10 2016 106 103.4

(51) Int. Cl.
*H01L 51/00* (2006.01)
*H01L 51/50* (2006.01)
(Continued)

(52) U.S. Cl.
CPC ........ *H01L 51/0059* (2013.01); *C07C 225/22* (2013.01); *C07C 255/58* (2013.01);
(Continued)

(58) Field of Classification Search
CPC . C07C 487/08; C07C 2603/30; C07C 255/58; Y02E 10/549; H01L 51/5012;
(Continued)

(56) References Cited

U.S. PATENT DOCUMENTS 5,238,936 A * 8/1993 Regnier ................. A61P 35/00
514/245
2015/0236274 A1* 8/2015 Hatakeyama ....... H01L 51/0054
257/40

(Continued)

FOREIGN PATENT DOCUMENTS

JP    2010024149 A    2/2010
JP    2010024149    *  4/2010
(Continued)

OTHER PUBLICATIONS

Machine Translation of JP2010024149 (Year: 2010).*
(Continued)

*Primary Examiner* — Andrew K Bohaty
*Assistant Examiner* — Jenna N Chandhok
(74) *Attorney, Agent, or Firm* — Hamre, Schumann, Mueller & Larson, P.C.

(57) ABSTRACT

The invention relates to purely organic emitter molecules of a new type according to formula I and to the use thereof in optoelectronic devices, in particular in organic light-emitting diodes (OLEDs), comprising donor D: an aromatic or
(Continued)

HOMO

LUMO heteraromatic chemical group on which the HOMO is located and which optionally has at least one substitution; acceptor A: an aromatic or heteromatic chemical group on which the LUMO is located and which optionally has at least one substitution; bridge B1, bridge B2: organic groups that link the donor D and the acceptor A in a non-conjugated manner; wherein in particular the energy difference $\Delta E(S_1-T_1)$ between the lowest excited singlet (S1) state of the organic emitter molecule and the triplet (T1) state of the organic emitter molecule lying thereunder is less than 2000 $cm^{-1}$.

4 Claims, 9 Drawing Sheets

(51) Int. Cl.

| | |
|---|---|
| *C09K 11/06* | (2006.01) |
| *C07D 413/04* | (2006.01) |
| *C07D 219/02* | (2006.01) |
| *C07D 221/16* | (2006.01) |
| *C07C 317/36* | (2006.01) |
| *C07D 209/86* | (2006.01) |
| *C07D 471/14* | (2006.01) |
| *C07D 241/46* | (2006.01) |
| *C07D 455/03* | (2006.01) |
| *C07C 255/58* | (2006.01) |
| *C07D 487/08* | (2006.01) |
| *C07C 225/22* | (2006.01) |
| *C07D 265/38* | (2006.01) |
| *C07D 321/12* | (2006.01) |
| *C07D 471/04* | (2006.01) |

(52) U.S. Cl.
CPC .......... *C07C 317/36* (2013.01); *C07D 209/86* (2013.01); *C07D 219/02* (2013.01); *C07D 221/16* (2013.01); *C07D 241/46* (2013.01); *C07D 265/38* (2013.01); *C07D 321/12* (2013.01); *C07D 413/04* (2013.01); *C07D 455/03* (2013.01); *C07D 471/04* (2013.01); *C07D 471/14* (2013.01); *C07D 487/08* (2013.01); *C09K 11/06* (2013.01); *H01L 51/005* (2013.01); *H01L 51/0051* (2013.01); *H01L 51/0072* (2013.01); *H01L 51/5012* (2013.01); *C07C 2603/24* (2017.05); *C07C 2603/30* (2017.05); *C07C 2603/36* (2017.05); *C07C 2603/86* (2017.05); *C09K 2211/1007* (2013.01); *C09K 2211/1014* (2013.01); *C09K 2211/1029* (2013.01); *C09K 2211/1033* (2013.01); *C09K 2211/1044* (2013.01); *C09K 2211/1088* (2013.01); *Y02E 10/549* (2013.01)

(58) Field of Classification Search
CPC ............. H01L 51/0059; H01L 51/005; H01L 51/0072; C09K 11/06
See application file for complete search history.

(56) References Cited

U.S. PATENT DOCUMENTS

2016/0380203 A1* 12/2016 Jenekhe ............ H01L 51/0072
252/500
2018/0212158 A1* 7/2018 Aspuru-Guzik ..... C07D 519/00

FOREIGN PATENT DOCUMENTS

| KR | 20120047038 A | 5/2012 |
|---|---|---|
| WO | 2015103215 A1 | 7/2015 |
| WO | WO-2015175678 A1 * | 11/2015 |

OTHER PUBLICATIONS

Chao et al., "Spirally configured cis-stilbene/fluorene hybrids as bipolar, organic sensitizers for solar cell applications", Chemical Communications, vol. 48, Jan. 1, 2012, pp. S1-S34, 34 pages.
International Search Report (English and German) and Written Opinion issued in PCT/EP2016/068037 dated Nov. 9, 2016, 16 pages.
Parker et al., "Triplet-Singlet Emission in Fluid Solutions Phosphorescence of Eosin", Transactions of the Faraday Society, 1971, vol. 67, pp. 1894-1904, 11 pages.
Lyakh et al., "Multireference Nature of Chemistry: The Coupled-Cluster View", Chemical Reviews, Dec. 28, 2011, pp. 182-243, 62 pages.
Szalay et al.; "Multiconfiguration Self-Consistent Field and Multireference Configuration Interaction Methods and Applications", Chemical Reviews, Dec. 28, 2011, pp. 108-181, 74 pages.
Czerwieniec et al., "Highly efficient thermally activated fluorescence of a new rigid Cu(I) complex [Cu(dmp) (phanephos)]++", Dalton Transactions, Issue 27, 2013, 5 pages.
Baleizao et al., "Thermally activated delayed fluorescence as a cycling process between excited singlet and triplet states: Application to the fullerenes", The Journal of Chemical Physics, published May 31, 2007, total 9 pages.
Prokhorov et al., "Brightly Luminescent Pt(II) Pincer Complexes with a Sterically Demanding Carboranyl-Phenylpyridine Ligand: A New Material Class for Diverse Optoelectronic Applications", Journal of The American Chemical Society, Published Jun. 17, 2014, pp. 9637-9642, 6 pages.

* cited by examiner

HOMO                    LUMO

HOMO  LUMO

HOMO  LUMO

ORGANIC MOLECULES HAVING TWO NON-CONJUGATED BRIDGES BETWEEN A DONOR AND AN ACCEPTOR FOR EFFECTIVE THERMALLY ACTIVATED DELAYED FLUORESCENCE FOR USE IN OPTOELECTRONIC DEVICES

The present invention relates to organic molecules used for optoelectronic devices and optoelectronic devices containing such organic molecules. The organic molecule has a donor unit and an acceptor unit, and the spatial positions of the donor unit and acceptor unit are linked to each other by two organic non-conjugated bridges. The organic molecules have a singlet state-triplet state narrow band gap required to effectively delay fluorescence, making the molecule particularly suitable for optoelectronic devices.

ABSTRACT

The invention relates to purely organic emitter molecules of a new type according to formula I and to the use thereof in optoelectronic devices, in particular in organic light-emitting diodes (OLEDs), comprising donor D: an aromatic or heteraromatic chemical group on which the HOMO is located and which optionally has at least one substitution; acceptor A: an aromatic or heteromatic chemical group on which the LUMO is located and which optionally has at least one substitution; bridge B1, bridge B2: organic groups that link the donor D and the acceptor A in a non-conjugated manner; wherein in particular the energy difference $\Delta E(S_1-T_1)$ between the lowest excited singlet (S1) state of the organic emitter molecule and the triplet (T1) state of the organic emitter molecule lying thereunder is less than 2000 cm$^{-1}$.

BACKGROUND ART

For many optoelectronic applications, luminescent molecules(=emitter molecules) should have an emission decay time τ that is as short as possible and a high photoluminescence quantum efficiency $Ø_L$. In addition, during the emission process, the applications of molecules without a metal complex, such as the inclusion of electrons in the lowest-excited triplet state T1 and the use of pure organic emitter molecules, are of great significance. Thermally-activated delayed fluorescence (TADF) can be generated at room temperature by setting a sufficiently small energy difference $\Delta E$ $(S_1-T_1)$ between the T1 state and the singlet state $S_1$ above it (FIG. 1) to meet the stated requirements. This process is known to those skilled in the art (refer to, for example, A. Parker, C. G. Hatchard; Trans. Faraday, Royal Society of Chem. 1961, 57, 1894), also called frequency boosting based on E type (because found firstly in eosin). As a result, it is possible to achieve effective TADF, that is, a decay time (TADF) of the emission decreases by several orders of magnitude compared to the phosphorescence decay time τ ($T_1$) when a long-lived triplet state is involved. In addition, significant increase in emission quantum efficiency $Ø_{PL}$ can be achieved in many cases, because the rapid return of competition occupies the process $T_1 \rightarrow k_B T \rightarrow S_1$, reducing the non-radiative process of the $T_1$ state (shown by the wavy lines in FIG. 1).

It is known from the prior art that, for many molecules with a transition in charge (CT) between the donor (D) fragment and the receptor (A) fragment, TADF may occur. However, the energy difference $\Delta E(S_1-T_1)$ found to date is still obviously large, therefore, photophysical properties desired by many applications, such as short decay time τ(TADF), have not been achieved yet.

SUMMARY OF THE INVENTION

Surprisingly, it is possible to find a method (molecular structure principle) which helps to reduce energy difference $\Delta E$ $(S_1-T_1)$ in a targeted manner to provide the corresponding pure organic molecules. According to equation (1), the energy difference is approximately proportional to the exchange integral of the quantum mechanics, $$\Delta E(S_1-T_1) \approx \text{const.} < \Psi D(r_1) \Psi A^*(r_2) | r_{12}^{-1} | \Psi D(r_2) \Psi A^*(r_1) > \quad (1)$$

Here, $r_1$ and $r_2$ are the electronic coordinates, and $r_{12}$ is the distance between the electron 1 and the electron 2. $\Psi_D$ is the wave function of the HOMO (highest occupied molecular orbit). For this type of molecules, HOMO is mainly distributed in the donor portion (D) of the molecule, while $\Psi_A^*$ represents LUMO (lowest unoccupied molecular orbit), mainly distributed in the receptor portion (A) of molecule. According to the equation (1), if the product $\Psi_D(r_1)\Psi_A^*(r_2)$ of wave function becomes small, $\Delta E$ $(S_1-T_1)$ becomes small. This requirement is not reached for a variety of molecules with intramolecular CT transitions, because the spatial expansion of the wave function $\Psi_D(r_1)$ and the excessive overlap of $\Psi A^*(r_2)$ result in excessively large $\Delta E(S_1-T_1)$ value. According to the invention, a molecular structure having significantly reduced wave function superimposition is proposed. This is achieved by a molecular structure in which non-conjugated, small chemical groups (bridges) separate donor and acceptor moieties, thus, significantly reducing expansion of HOMO into the receptor area and expansion of LUMO into the donor region.

The formula I shows the molecular structure of the organic molecules according to the invention. There are two organic bridges between the donor and acceptor fragments. By appropriatetly selecting these bridges, the spatial superposition of HOMO (mainly on the donor) and LUMO (mainly on the acceptor) can be significantly reduced. In order not to make the transition probability between the electronic ground state $S_0$ and the excited state $S_1$ too small, slight overlap of the rails is of great significance. In addition, double bridging causes the molecules to harden, achieving an increase of emission quantum efficiency and a decrease of half-value width of emission. In many cases, the decrease of half-value width of emission is of great significance to acquire a definite emtting color (color purity), for example, luminescence in OLEDs.

The formula I shows the molecular structure of one embodiment of an organic molecule with two chemical bridges according to the present invention. These bridges significantly reduce the conjugation between D and A and the overlap of HOMO and LUMO and stabilize the molecular structure.

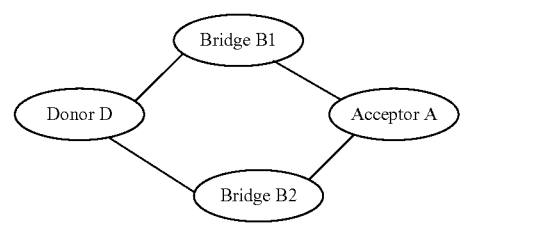

Formula I

Formula I: it represents the molecular structure of an organic molecule according to the invention. The organic molecule consists of an aromatic or heteroaromatic donor fragment D and an aromatic or heteroaromatic receptor fragment A bound by two unconjugated bridges B1 and B2. The bridges reduce the apparent overlap between the donor-HOMO and the acceptor-LUMO.

For optoelectronic applications that require a small value of $\Delta E$ ($S_1-T_1$), it is important that fragments D and A each have a sufficiently high donor or acceptor intensity. (These terms are well known to those skilled in the art.) The corresponding intensity can be described by the intensity of the electron donating (for the donor) or the intensity of electron withdrawing (for the receptor).

By choosing the appropriate molecular structure, the energy difference $\Delta E$ ($S_1-T_1$) value can be made to be less than 2,000 $cm^{-1}$, in particular less than 1,500 $cm^{-1}$ or preferably less than 800 $cm^{-1}$ or even more preferably less than 400 $cm^{-1}$ or in particular less than 200 $cm^{-1}$. The corresponding value is determined by a single molecule. The value can be determined by different methods.

The value of $\Delta E$ ($S_1-T_1$) is calculated from quantum mechanics, for example, using a commercially available TD-DFT program (e.g. Gaussian 09 program) or a free version of NWChem (e.g. version 6.1), CC2 method (TURBOMOLE GmbH, Karlsruhe) or CAS methods (complete active state method). (refer to D. I. Lyakh, M. Musiaz, V. F. Lotrich, R. J. Bartlett, Chem. Rev. 2012, 112, 182-243 and P. G. Szalay, T. Muller, G. Gidofalvi, H. Lischka, R. Shepard, Chem. Rev. 2012, 112, 108-181). An example of calculation is given in the embodiments.

$\Delta E$ ($S_1-T_1$) value can also be determined experimentally. The organic molecules according to the present invention exhibit not only instantaneous (=spontaneous) fluorescence components (decay time: several to dozens of nanoseconds), but also exhibit TADF attenuation components with attenuation ranging from one hundred to several hundred. A commercially available device can be used to determine the relevant decay time as a temperature function. By using the equation (2), the $\Delta E(S_1-T_1)$ value can be determined by fitting the experimental curve according to the temperature change of the emission decay time [refer to, for example, Czerwieniec R., Kowalski K., Yersin H.; Dalton Trans. 2013, 42, 9826]:

$$\tau(t) = \frac{3 + \exp(-\Delta E(S_1 - T_1)/k_B T)}{3/\tau(T_1) + 1/\tau(S_1)\exp(-\Delta E(S_1 - T_1)/k_B T)} \qquad (2)$$

Here, $\tau(T)$ is experimentally determined and, if necessary, it is the average decay time after instantaneous emission decay and thermal equilibrium (several hundred nanoseconds). $\tau(S_1)$ is the emission decay time in the $S_1$ state. Other parameters have been defined earlier.

For many applications, the luminous decay time $\tau(TADF)$ (=$\tau(300K)$) should be as small as possible (as small as less than hundreds of $\mu$s). In order to achieve this, it is significant to increase the spin-orbit-couple (SBK) effect between the T1 state and the higher molecular energy state, in addition to setting a small $\Delta E$ ($S_1-T_1$) value for obtaining greater intersystem crossing rate (ISC). For this purpose, the donor fragment D and/or acceptor fragment A can be replaced, for example, with halogen Cl, Br and/or I.

For the molecules of the present invention, an intersystem crossing jump (ISC) rate can be increased. The molecules in the invention have localized states with energies very close to the CT state at donor D and/or acceptor A. (In the case of a local triplet state where the energy is lower than the charge transfer (CT) state, the number of the triplet state changes, for example, the local state is called T1 and the CT-state is called T2). The rate is increased due to SBK enhancement based on quantum mechanics mixing between these states. The target molecule is identified using known computer programs or quantum mechanical methods (eg, Gaussian 09 or CC2 methods). The energy gap between the above states is less than 2000 $cm^{-1}$, in particular less than 1500 $cm^{-1}$, more preferably less than 1000 $cm^{-1}$, further more preferably less than 400 $cm^{-1}$ and most preferably less than 200 $cm^{-1}$. Mutual energy shifts can be achieved by changing the donor and/or acceptor intensity and changing electron donating substitution of donors and/or changing the electron withdrawing substitution of acceptors. Energy shifts can also be achieved by more than one substitutions of electron donating and/or electron withdrawing. The CT state shift can also be achieved by changing the polarity of the environment (e.g. polymer matrix).

The chemical bridges B1 and B2 between segments D and A not only have the effect of enhancing the rigidity of the molecules, but also surprisingly increase the emission quantum efficiency $\varnothing_L$.

In addition, these bridges strongly restrict the free migration of donor molecule fragment D relative to acceptor molecule fragment A. Thus, the variation of the $\Delta E(S_1-T_1)$ value for a given emitter molecule incorporated into the polymer matrix, i.e., the non-uniformity of this value, is greatly limited, thereby significantly reducing the long emission decay time in the long-life "decay tail" area often occurring in the prior art. In addition, the color purity of the emission is improved by reducing the half width of the emission band.

Description of Receptor a and Donor D in Formula I

The emitter molecule of Formula I consists of two fragments covalently linked by two bridges B1, B2, i.e. donor fragment D and acceptor fragment A. The donor fragment and acceptor fragment are composed of aromatic or heteraromatic groups, or other alternatives. The bridges B1, B2 are short aliphatic or heteroaliphatic segments that greatly reduce the conjugation (delocalization) between the aromatic segments A and D.

The chemical structures of the molecular fragments A and D are described in combination with the formulas II and III.

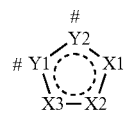

Formula II

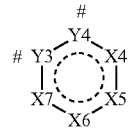

Formula III

Formulas II and III: Structures of D and A molecular fragments. The donor and acceptor fragments consist of different aromatic/heteroaromatic fragments, which, independently of one another, can be five- or six-membered ring systems, and can be substituted or expanded (with Fused Aromatic Ring). The donor or acceptor fragments can be obtained depending on the individual structure.

marked site. The donor moiety D or acceptor moiety A binds to B1 and B2 via this site. The connotations of groups X1 to X7 and Y1 to Y4 will be explained below.

Y1, Y2, Y3 and Y4 are C or N, independently of each other.

X1 to X7 are N, O, S, Se, CH, NH, C—R1 or N—R2, independently of each other. Wherein R1 and R2 groups are independently selected from —H, alkyl (e.g. methyl, ethyl, n-propyl, isopropyl, n-butyl, isobutyl, tert-butyl, adamantyl), cycloalkyi (e.g. cyclopropyl, cyclopentyl, cyclohexyl), alkenyl (e.g. vinyl, allyl), alkynyl (e.g. ethynyl), aryl (e.g. phenyl, tolyl, naphthyl), heteroaryl (e.g. furyl, thienyl, pyrrolyl), chemically substituted alkyl, alkenyl, alkynyl, aryl, or heteroaryl, alkoxy (—OR'), thioalkyl (—SR'), sulfonyl (—SO2R), acyl (—COR'), formyl (—CHO), carboxyl (—CO2R'), boryl (—BR'R"), sulfinyl (—SOR'), amine (—NR'R"), phosphino (—PR'R"), phosphinyl (—POR'R"), amido (—NR'COR), silyl (—SiR'R"R'), cyano and (—CN), nitro (—NO2), nitroso (—NO), isocyanato (—NCO), thiocyano (—NCS) or halogen (—F, —Cl, —Br, —I). The residues R', R" and R'" are defined as R1 and R2. The residues R', R" and R'" can be covalently linked to each other, so that aliphatic, heteroaliphatic or unsaturated ring systems can also be formed.

In addition, the group R1 or R2 can be alkyl-$C_nH_{n+1}$ ($1 \leq n \leq 8$, particularly $1 \leq n \leq 4$), cycloalkyl-$C_nH2_{n-1}$ ($3 \leq n \leq 6$), substituted alkyl/cycloalkyl, alkoxy-$OC_nH_{2n+1}$ ($1 \leq n \leq 8$, particularly $1 \leq n \leq 4$), thioalkyl-$SC_nH2_{n+1}$ ($1 \leq n \leq 8$, particularly $1 \leq n \leq 4$), or alkylated amine groups, —$N(C_nH_{2n+1})(C_{n'}H_{2n'+1})$ (n and n'=1 to 8, particularly 1, 2, 3) or —$N(C_{n''}H2_{n''-1})(C_{n'''}H2_{n'''-1})$ (n" and n'"=3, 4, 5 or 6, particularly 5 or 6).

The pendant groups (R1 and R2) of fragments X1 to X3 or X4 to X7 of the respective molecular moiety (donor D, acceptor A) can be linked together in such a way as to form other aliphatic, aromatic or (hetero) aromatic ring systems.

Some embodiments of the molecules according to the invention have two ring systems of the formula II or two ring systems of the formula III, which may be the same or different. If the ring systems are the same, these ring systems have different substitution patterns.

In a specific embodiment, the aromatic or heteroaromatic rings belonging to the donor and acceptor segments linked by two bridges B1, B2 are not fused with other aromatic or heteroaromatic rings; in this embodiment, donor fragment d and receptor fragment A have only one aromatic or heteroaromatic ring respectively.

In one embodiment of the invention, in order to increase spin-orbit coupling, the bridges of aromatic and/or heteroaromatic ring systems or organic molecules with halogen (Cl, Br or I).

Molecular systems according to Formula II (five-membered ring system) and Formula III (six-membered ring system) can effectively act as donors or acceptors. In order to achieve a specific donor effect, the HOMO must be electron-rich zone and mainly located on the donor moiety. In order to achieve a specific receptor effect, LUMO must be electron-deficient zone and mainly located on the acceptor moiety. The orbital schematic shown in FIG. 2 should illustrate the energy preconditions for achieving a D-A-emitter molecule according to the present invention.

Generally, the HOMO and LUMO energies of the respective donor and acceptor moieties can be determined electrochemically. In order to realize the substance having the orbital characteristics as shown in FIG. 2, the following conditions must be satisfied: (1) the oxidation potential of the donor fragment is smaller than the oxidation potential of the acceptor fragment: $E_{OX}(D) < E_{OX}(A)$ ($E_{OX}$=oxidation potential), (2) the reduction potential of the receptor fragment is greater than the reduction potential of the donor fragment: $E_{RED}(D) < E_{RED}(A)$ ($E_{RED}$=reduction potential). The redox properties of many conventional aromatics can be available from the following references[[M. Montalti, A. Credi, L. Prodi, M. T. Gandolfi, Handbook of Photochemistry, 3rd ed., CRC Tayler & Francis, Boca Raton, 2006]. Correspondingly, electron-excited states occur in donor-acceptor molecules, which are characterized by a marked shift of the electron density from the donor to the acceptor as compared to the molecules of the ground state ($S_0$). This state is called Charge Transfer (CT) state. As is well known to those skilled in the art, this results in the excitation singlet state $^1CT$ (corresponding to the $S_1$ state as defined above) and the excitation triplet state $^3CT$ (corresponding to the $T_1$ state as defined above).

Electron-rich donor fragments or electron-deficient acceptor fragments can be achieved by introducing specific heteroatoms into the fused ring system and/or by performing specific substitutions with electron donating or electron withdrawing functional groups. Therefore, introducing heteroatoms, typically nitrogen (forming aza-aromatics) in aromatic six-membered rings will affect the stability of the π and π* orbitals based on the mediation effect known to those skilled in the art. As a result, the mono-electron reduction and oxidation potentials of the azaaromatics are higher than the redox potentials of the corresponding pure aromatic (non-heteroatom) hydrocarbons. In the aromatic five-membered system, the introduction of heteroatoms, usually nitrogen, destabilizes the π and π* orbitals through the mesomeric effect, resulting in lower oxidation and reduction potentials. Additional orbital energy modulation is achieved by either electron withdrawing (EWG=electron withdrawing group) or electron donating (EDG=electron donating group) functional groups. EWG substitutions generally result in lower HOMO and LUMO energies, whereas EDG substitutions generally result in higher HOMO and LUMO states. Generally the following EWG or EDG are used: [M. Smith, J. March; March's Advanced Organic Chemistry, Reaction, Mechanism and Structure, 6th ed. John Wiley & Sons, Inc., Hoboken, N.J., 2007]

EDG Example:
—NR'R", —NHR', —OR', -alkyl, —NH(CO)R', —O(CO)R', -(hetero)aryl, —(CH)CR'R", phenoxazinyl, phenothiazinyl, carbazolyl, dihydrophenylhydrazinyl, all aryl and heterocyclic groups may optionally be substituted by other alkyl and/or aryl groups and/or F, Cl, Br and/or I. (If necessary, apply to increase SBK). R' and R" are defined as above.

For selected EDG substitutions, it is also possible to determine the donor intensity (EDG intensity) arrangement:

Strong-intensity electron donors: —$O^-$, —$N(CH_3)_2$, —$N(C_6H_5)_2$, phenoxazinyl, phenothiazinyl, carbazolyl, —$NHCH_3$;

Medium-intensity electron donors: —$OC_6H_5$, —$OCH_3$, —$NH(CO)CH_3$;

Weak-intensity electron donors: aryl, —$C(CH_3)_3$, —$CH_3$.

EWG Example:
Halogen, —COR', —$CO_2R$, —$CF_3$, —BR'R", —$BF_2$, —CN, —$SO_3R$, —$NH_3^+$, —$(NR'R"R''')^+$, alkyl group. R', R" and R'" are defined as above.

For selected EWG substitutions, the acceptor intensity (EWG intensity) arrangement can be given:

Strong electron-withdrawing: —$NO_2$, —$CF_3$, —CH$(CN)_2$, —CN;

Medium electron-withdrawing: —$SO_3CH_3$, —$COCH_3$, —CHO; —F

Weak electron-withdrawing: —Cl, —Br, —I. (If necessary, apply to increase SBK).

In one embodiment, the donor fragment D is selected from substituted aromatic five-membered rings or substituted aromatic six-membered rings, wherein the five- and/or six-membered rings have at least one electron donating substituents (EDG) (pendant group at X1 to X3 or X4 to X7) and/or have one or more heteroatoms such as Y1, Y2, X1, X2, or X3=N in a five-membered ring system. It is also preferred to use at least one EDG for substitution if the pendant group linkage at X1, X2 and X3 or X5, X6 and X7 results in the condensation system expanding to an additional aromatic ring.

In one embodiment, the acceptor fragment A is selected from substituted aromatic five-membered rings or substituted aromatic six-membered rings, wherein the five- and/or six-membered rings have at least one electron withdrawing substituents (EDG) (pendant group at X1 to X3 or X4 to X7) and/or have one or more heteroatoms such as Y3, Y4, X4, X5, X6 or X7=N in a six-membered ring system. It is also preferred to use at least one EWG for substitution if the pendant group linkage at X1, X2 and X3 or X4, X5, X6 and X7 results in expanding to an additional aromatic ring.

As described above, both the donor fragment D and acceptor fragment A may have fused rings. The number of donor and/or acceptor conjugated rings is less than four. In ring systems with a conjugate ring number greater than 1 (but less than or equal to 3), it may be necessary to choose substitutions that have stronger electron-withdrawing effects on the donor fragments and/or have stronger electron-withdrawing effects on the acceptor fragments.

In one embodiment, bridges B1 and B2 have a structure as defined by formulas IV and V, wherein the bridges B1 and B2 may be the same or different.

$$\#A1\#$$ Formula IV $$\#A2-A3\#$$ Formula V

The symbol # indicates the linkage with the molecule donor or acceptor moiety. A1 to A3 represent fragments of bridges B1 and B2, wherein the fragment of the bridges B1 and B2 with the same name can be same or different.

Chemical group A1 is:

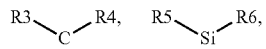

O, S or

wherein the chemical groups R3-R7 are defined as above R1 and R2.

Chemical groups A2 and A3 are:
A2:

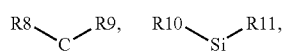

O, S or

A3:

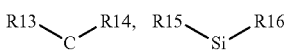

O, S or

In addition, one or more groups of A2 and A3 may be one of the following groups independently,

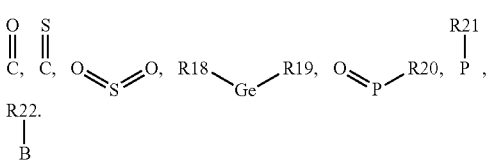

Groups R8 to R22 are defined as R1 and R2.

It is achieved to bridge the donor or acceptor via the atoms selected from C, N, Si, O, S, P, B and Ge, and the interconnection in the presence of multiple bridge elements A2 and A3 (Formula V).

DETAILED DESCRIPTIONS OF EMBODIMENTS

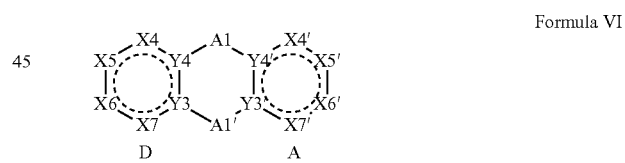
Formula VI

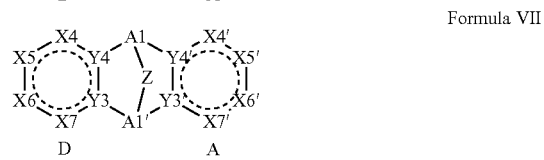
Formula VII

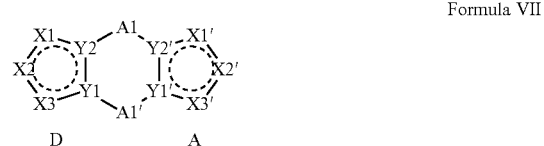
Formula VII

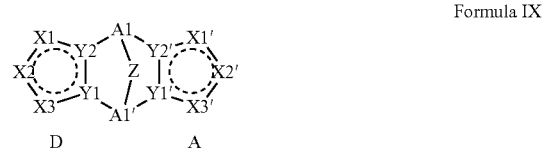
Formula IX

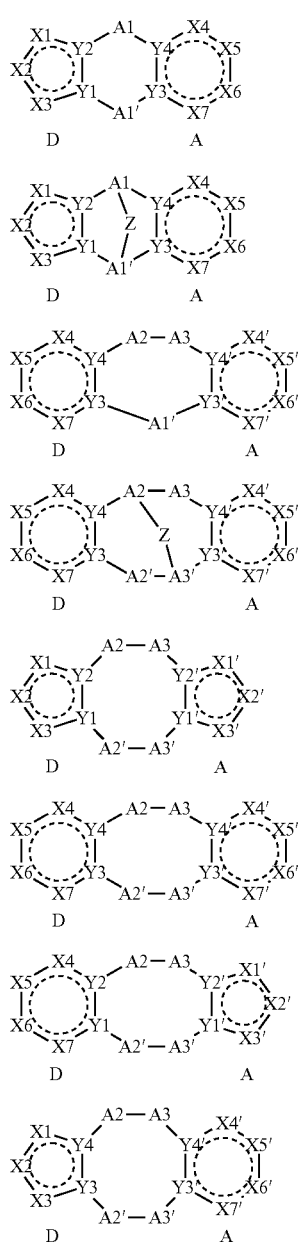

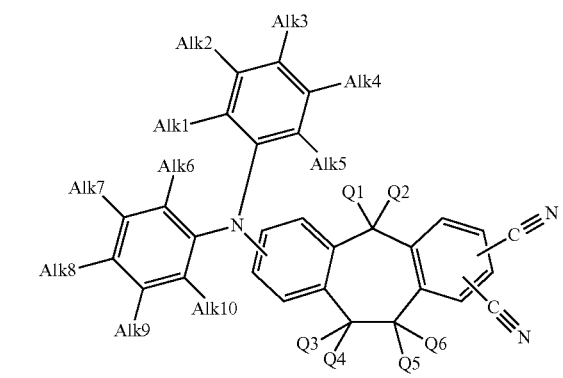

The molecular structure of the emitter material having the formula I according to the invention is further explained by means of the structural formulas VI to XVII. These structural formulas represent examples of emitter materials according to the invention. Y1'-Y4' and X1'-X7' are defined as Y1-Y4 and XI-X7 (formulas II and III). A1', A2', A3' groups are defined as A1 to A3. The bridge fragments A1 and A1', A2 and A2', A3 and A3', respectively, may be the same or different.

Additional bridging groups Z are, for example, —CH$_2$—, —C(CH$_3$)$_2$, —O—, —C$_6$H$_4$-(phenylene), —C$_5$H$_8$-(cyclopentylene), —CO-(carbonyl), —SO$_2$—, —N(CH$_3$)—. They represent the mutual connection of fragments A1 to A3 and A1' to A3' of bridges B1 and B2.

In a particular embodiment, the organic molecules according to the invention have a structure of Formula XVIII.

In the donor region, the emitter molecule has an aromatic amine group. The acceptor moiety is a dicyanophenyl group in which two CN-substituents may be ortho, meta or para to each other and may be adjacent to a bridged aliphatic group.

Q1 to Q6 are each independently selected from the group consisting of H, CH$_3$, C$_2$H$_5$, C$_3$H$_7$, C$_4$H$_9$, C$_5$H$_{11}$, C$_6$H$_{13}$, phenyl, tolyl, xylyl, benzyl, thienyl, oxazolyl, oxadiazolyl, triazolyl, tetrazolyl, oxazolyl, oxadiazolyl, furyl, and carbazolyl.

Q1 and Q2, Q3 and Q4, and Q5 and Q6 may be linked together to form a cycloalkyl- or aromatic spiro system (e.g., to stabilize the molecular structure).

Alk1 to Alk10 are H or a straight-chain or branched-chain (C$_n$H$_{2n+1}$; n=1, 2, 3, 4, 5, or 6) aliphatic group or a cycloalkyl group (C$_n$H$_{2n+1}$; n=5 or 6), independently of one another.

In addition, Alk1 and Alk6 can be omitted and the two benzene rings of the donor system are covalently bonded together to form a carbazole unit, as shown in Formula XIX.

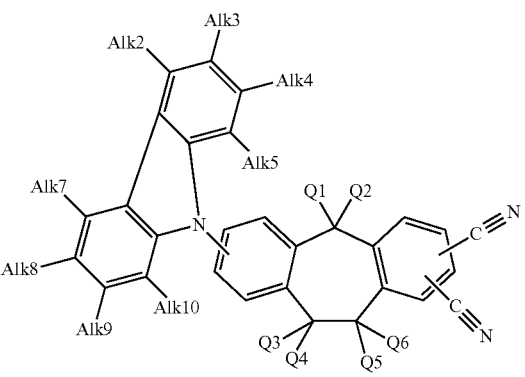

The formula XVIII illustrates the substituent.

EMBODIMENTS

The molecules in the following examples of the present invention may have at least one substitutions of Cl, Br and/or I to increase spin-orbit coupling (SBK). The appropriate position for substitutions can be determined by quantum mechanical calculations, and a computational program including SBK (eg, ADF, ORCA program) is used herein. To know the trend, DFT or CC2 calculation can be conducted, so as to identify the substitution position of halogen, i.e. the halogen atom orbitals with a significant proportion in HOMO, HOMO-1, HOMO-2 and/or LUMO, LUMO+1, LUMO+2. For the substitution pattern identified by this way, it should be noted that, for example, when calculated by TDDFT or CC2, the energy difference $\Delta E$ ($S_1$-$T_1$) of organic molecules between the lowest excited singlet state ($S_1$) and it below triplet state ($T_1$) is less than 2,000 cm$^{-1}$, in particular less than 1500 cm$^{-1}$, preferably less than 800 cm$^{-1}$, more preferably less than 400 cm$^{-1}$ and most preferably less than 200 cm$^{-1}$.

The materials in the present invention can be synthesized using catalytic coupling reactions (e.g. Suzuki coupling reactions, Buchwald-Hartwig cross-coupling reactions) or various condensation reactions that are known to those skilled in the art.

Embodiment 1

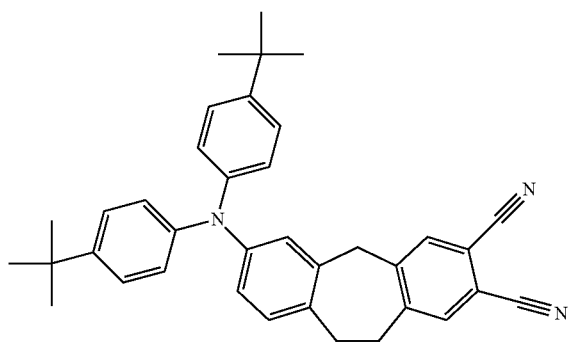 [SMILES: CC(C)(C)c1ccc(N(c2ccc(C(C)(C)C)cc2)c2ccc3c(c2)Cc2cc(C#N)c(C#N)cc2CC3)cc1]

Example Molecule 1

The molecules according to the invention shown in Example 1 would be detailed below. As shown from the frontier orbital in FIG. 3, the HOMO and LUMO were located in distinctly different spatial regions of the molecule. It was expected that the gap between the lowest triplet state and the singlet state above it was small enough that the molecule exhibited a significant TADF effect. The calculation of the example molecule 1 within the range of TD-DFT calculation (function B3LYP, basis set 6-31G (d, p)) showed that the energy level difference of the optimized triplet-state geometrical structure was $\Delta E(S_1$-$T_1)=75$ cm$^{-1}$. Therefore, the example molecule 1 was a good TADF emitter. The following reaction scheme illustrated the chemical synthesis of example molecule 1:

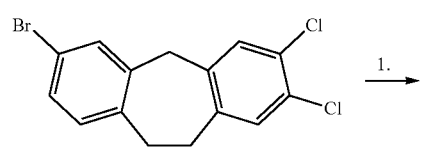

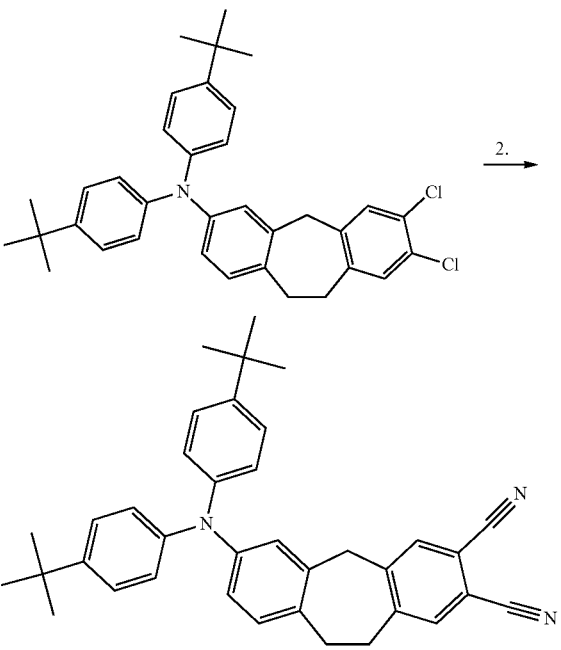

Reactants and reaction conditions:

(1) (t-$C_4H_9$—$C_6H_5$)$_2$NH, Pd($CH_3COO$)$_2$, P[(C($CH_3$)$_3$]$_3$, ($CH_3$)$_3$CONa, 90° C., 19 hours.

(2) $K_4$[Fe(CN)$_6$], Pd($CH_3COO$)$_2$, P[(C($CH_3$)$_3$]$_3$, $Na_2CO_3$, ($CH_3$)$_2$NCHO, 140° C., 12 hours.

Synthesis can be performed according to the following detailed reaction scheme:

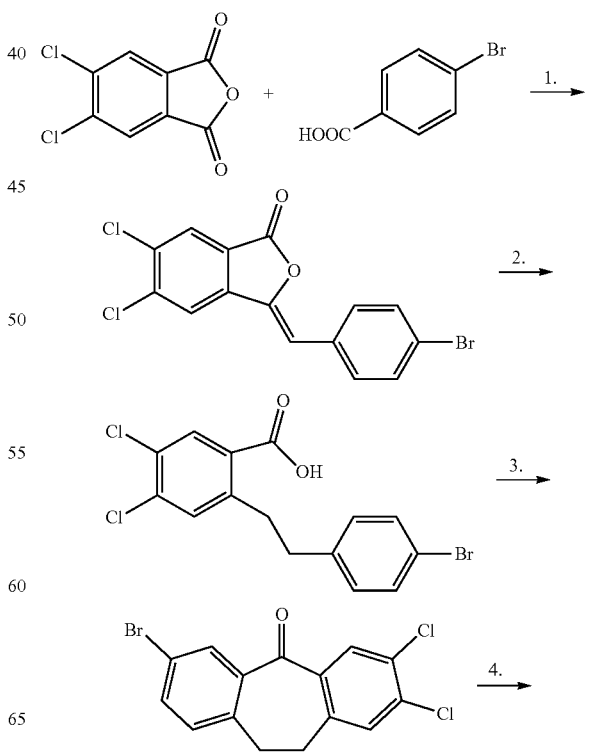

-continued

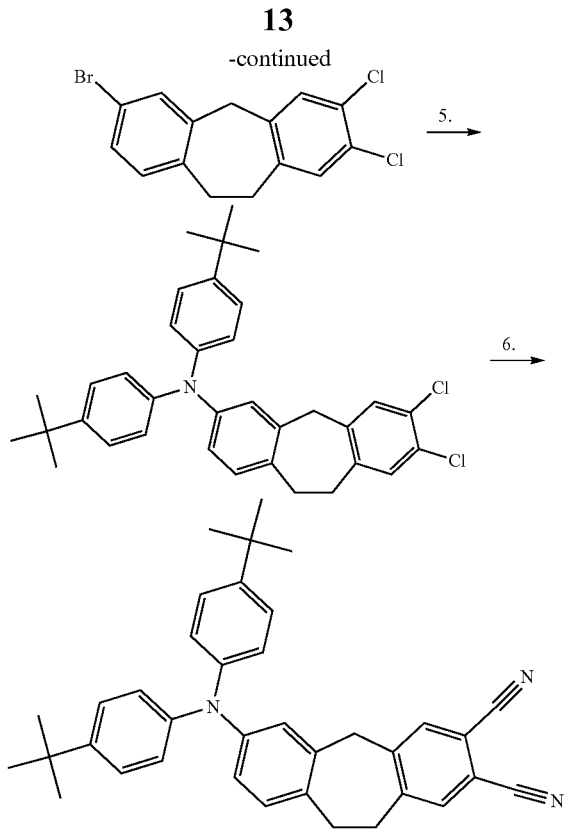

Reactants and reaction conditions:
(1) $CH_3CO_2Na$, 230° C., 3 hours
(2) $HPO_2$, $I_2$, red phosphorus, $CH_3COOH$, 80° C., 24 hours
(3) $(H_3PO_4)n$, 175° C., 5 hours
(4) $Al[OCH(CH_3)_2]_3$, 275° C., 3 hours
(5) $(t-C_4H_9-C_6H_5)_2NH$, $Pd(CH_3COO)_2$, $P[(C(CH_3)_3]_3$, $(CH_3)_3CONa$, 90° C., 19 hours
(6) $K_4[Fe(CN)_6]$, $Pd(CH_3COO)_2$, $P[(C(CH_3)_3]_3$, $Na_2CO_3$, $(CH_3)_2NCHO$, 140° C., 12 hours Chemical Analysis:
$R_f$(cyclohexane/ethyl acetate 10:1): 0.52. $^1H$ NMR ($CDCl_3$, 300 MHz, δ ppm): 1.31 (s, 18H), 3.13 (m, 4H), 4.05 (s, 2H), 6.84 (dd, J=3.6 Hz, J=12.0 Hz, 1H), 6.90 (s, 1H), 6.95 (s, 1H), 6.95 (d, J=9 Hz, 5H), 7.22 (d, J=9 Hz, 4H), 7.55 (s, 2H). 13C-NMR (300 MHz $CDCl_3$, δ ppm): 30.72 (CH2), 31.46 (CH3), 32.80 (CH2), 34.31 (CH2), 40.56 (Cquat), 113.16 (Cquat), 113.73 (Cquat), 115.59 (Cquat), 122.35 (Cquat), 123.48 (CH), 123.78 (CqUat), 126.03 (CH), 130.57 (CqUat), 130.94 (CH), 133.86 (CH), 134.48 (CH), 136.63 (Cquat), 144.91 (CqUat), 145.40 (Cquat), 145.69 (Cquat), 146.31 (Cquat).

MS (ES-MS=electrospray ionization mass spectrometry) m/z: 523 (M+). MS (HR-ES-MS=high resolution electrospray ionization mass spectrometer) m/z: $C_{37}H_{37}N_3$ Calculation: 523.2979, Measurement: 523.2980 (M+). $C_{37}H_{37}N_3$ Calculation: C 84.86, H 7.12, N 8.02%, Measurement: C 84.54, H 7.36, N 7.90%.

The example molecule 1 could be dissolved in many organic solvents such as methylene chloride ($CH_2Cl_2$), toluene, hexane, n-octane, tetrahydrofuran (THF), acetone, dimethylformamide (DMF), acetonitrile, ethyl alcohol, methanol, xylene or benzene. The excellent solubility in methylene chloride made polymethylmethacrylate (PMMA) or polystyrene (PS) doping possible.

The emitter material according to Embodiment 1 could be sublimated (temperature 170° C., pressure $10^{-3}$ mbar).

Photophysical measurements of example molecule 1 in PMMA or PS (doping concentration c≈1 wt %) demonstrated the occurrence of TADF and the favorable emission properties. At very low temperatures, for example when T=2K, thermal activation was not possible. Thus, the emission showed two very different decay times, namely, a very short component, which corresponded to an $S_1 \rightarrow S_0$-fluorescence transition, about 4 ns in PMMA, 25 ns in PS, and a very long component, which was classified as phosphorescence of $T_1 \rightarrow S_0$ transitions, τ(phos)≈550 ms in PMMA and τ(phos)≈450 ms in PS. (Note: nitrogen purging of samples)

FIG. 4 showed the corresponding time-resolved emission spectra in PS, i.e. no delay time (t=0 ns), detection time window Δt=100 ns, corresponding to short-term spectra of fluorescence, and corresponding to the long-term spectra of phosphorescence (t=500 and Δt=900 ms).

When the temperature rose to T=300K, drastic changes in spectra and decay behavior may occur, which would support the occurrence of TADF. FIG. 5 showed the short time domain (spontaneous fluorescence) and long time domain time-resolved emission spectra of example molecule 1 dissolved in PS. Since both spectra had approximately the same peak positions, long-lived components could also be interpreted as fluorescence-TADF emission in this case. The fluorescence decay time in PMMA was about 4 ns, and the fluorescence decay time in PS was about 25 ns. However, in PMMA, its long-lived component was greatly shortened to about 10 μs, and the long-lived component in PS was also shortened to about 10 μs.

It was of significance to compare the emission quantum efficiency at T=300K with the value obtained in ambient air under nitrogen purging (PMMA-doped samples). pL (nitrogen)=40%, pL (air)=25%. The result showed that the triplet state was involved in the emission process, because oxygen in the air usually only caused quenching of long-lived triplet states (A. M. Prokhorov et al, J. Am. Chem. Soc. 2014, 136, 9637). Since triplet state occupation was a prerequisite for generating TADF, this behavior again showed that example molecule 1 had the desired TADF properties. Notes: The emission maximum in PMMA at T=300K within the blue-white range was λ(max)=486 nm (CIE x: 0.198, y: 0.287), and the emission maximum in PS at T=300K within the blue range was λ(max)=450 nm (CIE x: 0.174; y: 0.154).

When studying substances dissolved in toluene, other photophysical properties of the emitter molecule according to Embodiment 1 can be identified. This further demonstrated that, for a simple measurement of the emitted quantum efficiency, as mentioned above, it was expected that the molecules dissolved in the toluene produced TADF because the emission quantum efficiency in air was significantly reduced. The corresponding measured values: $Ø_{PL}$(nitrogen)=30% and $Ø_{PL}$(air)=5%.

FIGS. 6a and 6b showed the emission attenuation behavior at T=300K in the ns region (FIG. 6a) and the μs region (FIG. 6b). Spontaneous fluorescence decayed with τ(fluorine)=60 ns. (FIG. 6a) In addition, there were two attenuation components of τ(TADF 1)=270 ns and τ(TADF 2)=9 μs. Both components were classified as TADF emissions.

FIG. 7 showed the time resolved emission spectra of example molecule 1 dissolved in toluene in three time domains, namely, the short time domain (spontaneous fluorescence) and two long time domains. These spectra were given of the attenuation components as shown in FIG. 6. Since all three spectra had the same peak position and the same spectral shape within the measurement accuracy range, the long-lived component could also be interpreted as fluorescence, i.e. two TADF emissions.

If the study was carried out in the non-phase-change temperature range of toluene and the sample that was remained liquid, the attenuation behaviors of the long-lived components emitted from example molecule 1 (concentration c≈10-$^5$ mol/l) dissolved in toluene could be obtained. A temperature range of about 200K to 300K was very suitable. The measured values of the corresponding attenuation components were shown as Arrhenius diagrams (Boltzmann diagrams) in FIG. 8. Using Equation 2, Equation 3 could be approximated as the experimentally derived emission decay time $\tau_{exp}$ (see C. Baleizao, M. N. Berberan-Santos, J. Chem. Phys, 2007, 126, 204510):

$$\ln\left(\frac{1}{\tau_{exp}}\right) = A - \frac{\Delta E_1 (S_1 - T_i)}{k_B T} \quad (3)$$

Where, A was a constant, i represented the TADF process 1 with ΔE1 activation energy in triplet state $T_1$ or TADF process 2 with activation energy ΔE2 in triplet state $T_2$.

The linear fitting of two time domain measurement points, ie two TADF emissions, was performed using Equation 3 according to FIG. 6. From the slope of the straight line, the activation energy could be obtained (ΔE[($S_1$-$T_1$), TADF1]=310 cm-$^1$ and ΔE [($S_1$-$T_2$), TADF2]=85 cm-$^1$).

When cooled to T=77K, the long-lived unstructured emissions was frozen. There was only one structured phosphorescence, the decay time was very long, τ(phos)=450 ms (not shown in the figure). However, for long-lived components, the structure of the spectrum could also be observed in FIG. 4. This spectral structure could be attributed to the emission of donor or acceptor fragments. No charge transfer (CT) transition was involved in this case. If it is assumed that the correlation 0-0 transition at the intersection of the energetic (extrapolated) sides of the emission curve is reflected by the abscissa, these spectra could be used to roughly estimate the energy difference associated with the occurrence of TADF. The result was that the ΔE was about (300±100) cm-$^1$, which also showed that the embodiment 1 was a TADF substance.

Therefore, the experiment demonstrated that the example molecule 1 produced TADF according to invention. The corresponding results of TADF behaviors for example molecule 1 doped in PMMA were also available.

It should be emphasized that this also showed that the energy difference 75 cm-$^1$ calculated for the CT transitions (see the description of FIG. 3) was very consistent with the activation energy of TADF 2 process determined in the experiments.

FIG. 9 schematically summarized the measurement results in a formal energy level diagram. The emission behavior of example molecule 1 was described by three excitation energy states. There was another triplet state T1 (Lok) that could be assigned to local emission under two CT states $5_1$ (CT) and $T_2$ (CT) with an experimentally determined energy difference of 85 cm$^{-1}$. The $S_1$ (CT) state showed transient spontaneous fluorescence and two emissions of long decay time but different time-lasting at room temperature, which were generated from the thermal activation of $T_2$ (CT) and $T_1$ (lok), respectively, thus representing different TADF emissions. The formal model described here was based on long-lived TADF components longer than 9 μs for the relaxation process between triplet states.

Here also illustrated one aspect for the naming of triplet state. It was based on the numbering by energy order, rather than by the type of electron excitation. Therefore, in the case of example molecule 1, the energy gap ΔE ($S_1$-$T_1$) between the CT states used was referred to as ΔE [$S_1$(CT)–$T_2$(CT)] due to the generation of the state $T_1$(Iok) of low energy.

Embodiment 2

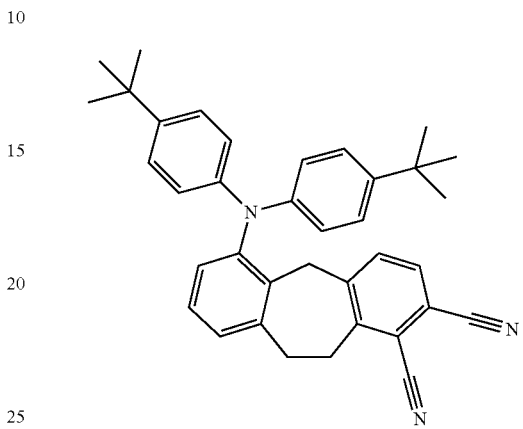

Example Molecule 2

The example molecule 2 according to the invention would be detailed below. As shown from the frontier orbital in FIG. 10, the HOMO and LUMO were located in distinctly different spatial regions of the molecule. It was expected that the gap between the lowest triplet state and the singlet state above it was small enough that the molecule exhibited a significant TADF effect. The calculation of the example molecule 2 within the range of TD-DFT calculation (function B3LYP, basis set 6-31G (d, p)) showed that the energy level difference of the optimized triplet-state geometrical structure was ΔE($S_1$-$T_1$)=85 cm-$^1$. Therefore, the example molecule 2 was a good TADF emitter. The following reaction scheme illustrated the chemical synthesis of example molecule 2.

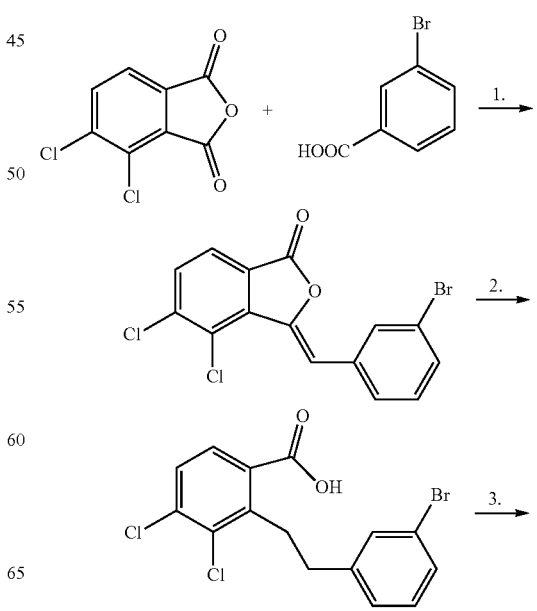

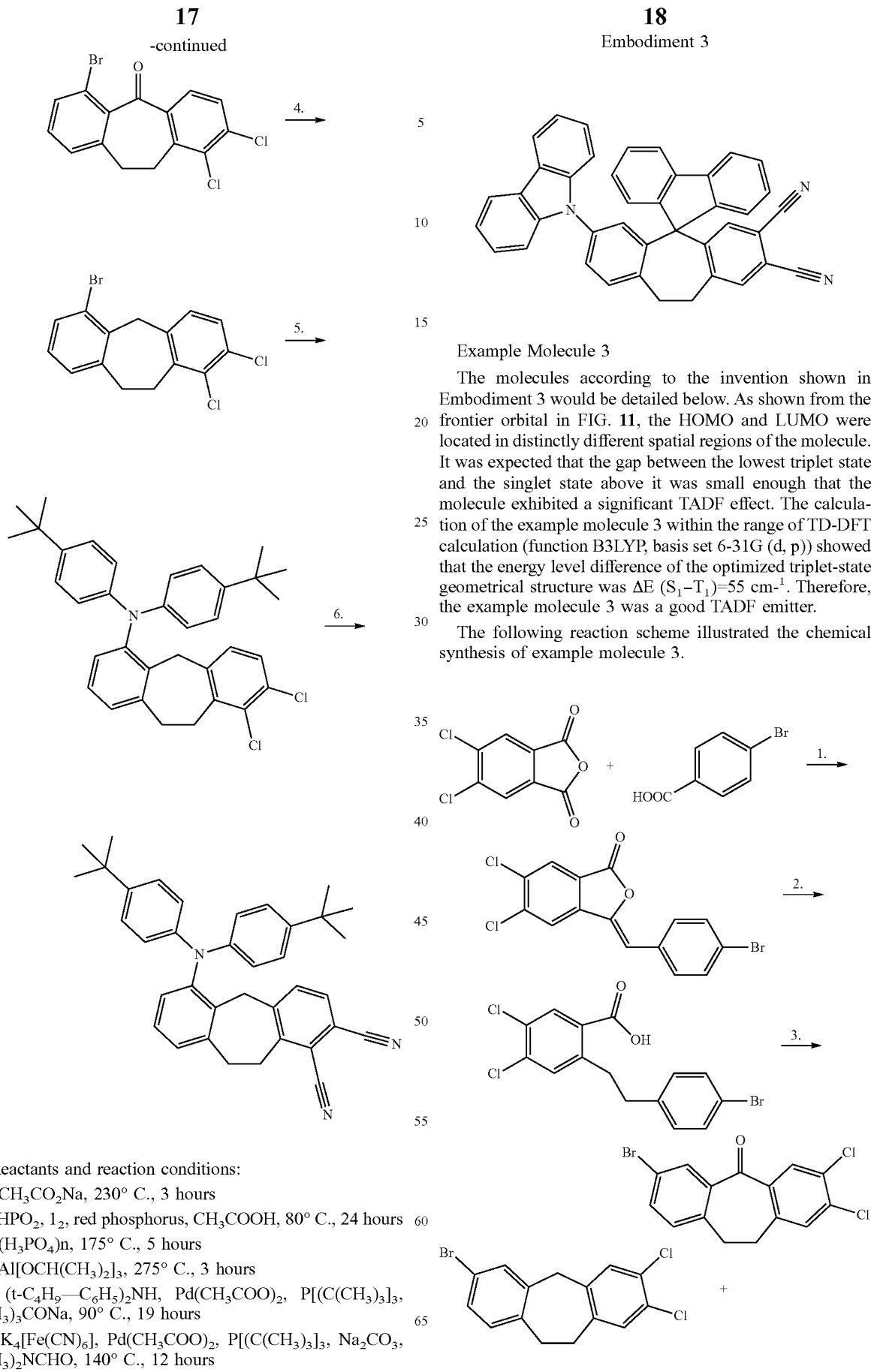

Embodiment 3

Example Molecule 3

The molecules according to the invention shown in Embodiment 3 would be detailed below. As shown from the frontier orbital in FIG. 11, the HOMO and LUMO were located in distinctly different spatial regions of the molecule. It was expected that the gap between the lowest triplet state and the singlet state above it was small enough that the molecule exhibited a significant TADF effect. The calculation of the example molecule 3 within the range of TD-DFT calculation (function B3LYP, basis set 6-31G (d, p)) showed that the energy level difference of the optimized triplet-state geometrical structure was $\Delta E\ (S_1-T_1)=55$ cm$^{-1}$. Therefore, the example molecule 3 was a good TADF emitter.

The following reaction scheme illustrated the chemical synthesis of example molecule 3.

Reactants and reaction conditions:
(1) CH$_3$CO$_2$Na, 230° C., 3 hours
(2) HPO$_2$, I$_2$, red phosphorus, CH$_3$COOH, 80° C., 24 hours
(3) (H$_3$PO$_4$)n, 175° C., 5 hours
(4) Al[OCH(CH$_3$)$_2$]$_3$, 275° C., 3 hours
(5) (t-C$_4$H$_9$—C$_6$H$_5$)$_2$NH, Pd(CH$_3$COO)$_2$, P[(C(CH$_3$)$_3$]$_3$, (CH$_3$)$_3$CONa, 90° C., 19 hours
(6) K$_4$[Fe(CN)$_6$], Pd(CH$_3$COO)$_2$, P[(C(CH$_3$)$_3$]$_3$, Na$_2$CO$_3$, (CH$_3$)$_2$NCHO, 140° C., 12 hours -continued

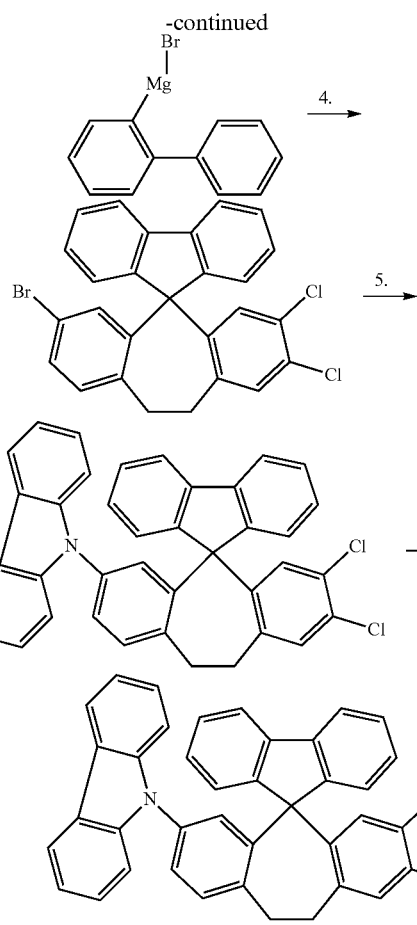

Reactants and reaction conditions:
(1) $CH_3CO_2Na$, 230° C., 3 hours.
(2) $HPO_2$, $I_2$, red phosphorus, $CH_3COOH$, 80° C., 24 hours
(3) $(H_3PO_4)n$, 175° C., 5 hours
(4) $(C_2H_5)_2O$, 30° C., 24 hours $NH_4Cl$, $H_2O$; $F_3CCO_2H$, 3 hours, 50° C.
(5) Carbazole, $Pd(CH_3COO)_2$, $P[(C(CH_3)_3]_3$, $(CH_3)_3CONa$, 90° C., 19 hours
(6) $K_4[Fe(CN)_6]$, $Pd(CH_3COO)_2$, $P[(C(CH3)_3]_3$, $Na_2CO_3$, $(CH_3)_2NCHO$, 140° C., 12 hours Embodiment 4

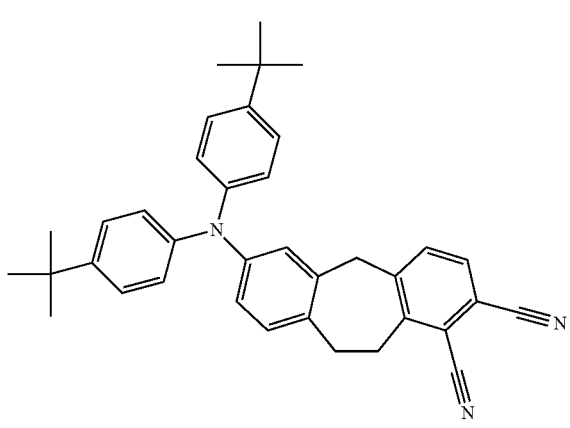 [SMILES: CC(C)(C)c1ccc(N(c2ccc(C(C)(C)C)cc2)c2ccc3c(c2)Cc2ccc(C#N)c(C#N)c2CC3)cc1]

Example Molecule 4

The example molecule 4 according to the invention would be detailed below. As shown from the frontier orbital in FIG. 12, the HOMO and LUMO were located in distinctly different spatial regions of the molecule. It was expected that the gap between the lowest triplet state and the singlet state above it was small enough that the molecule exhibited a significant TADF effect. The calculation of the example molecule 4 within the range of TD-DFT calculation (function B3LYP, basis set 6-31G (d, p)) showed that the energy level difference of the optimized triplet-state geometrical structure was $\Delta E(S_1-T_1)=88$ cm$^{-1}$. Therefore, the example molecule 4 was a good TADF emitter.

The following reaction scheme illustrated the chemical synthesis of example molecule 4.

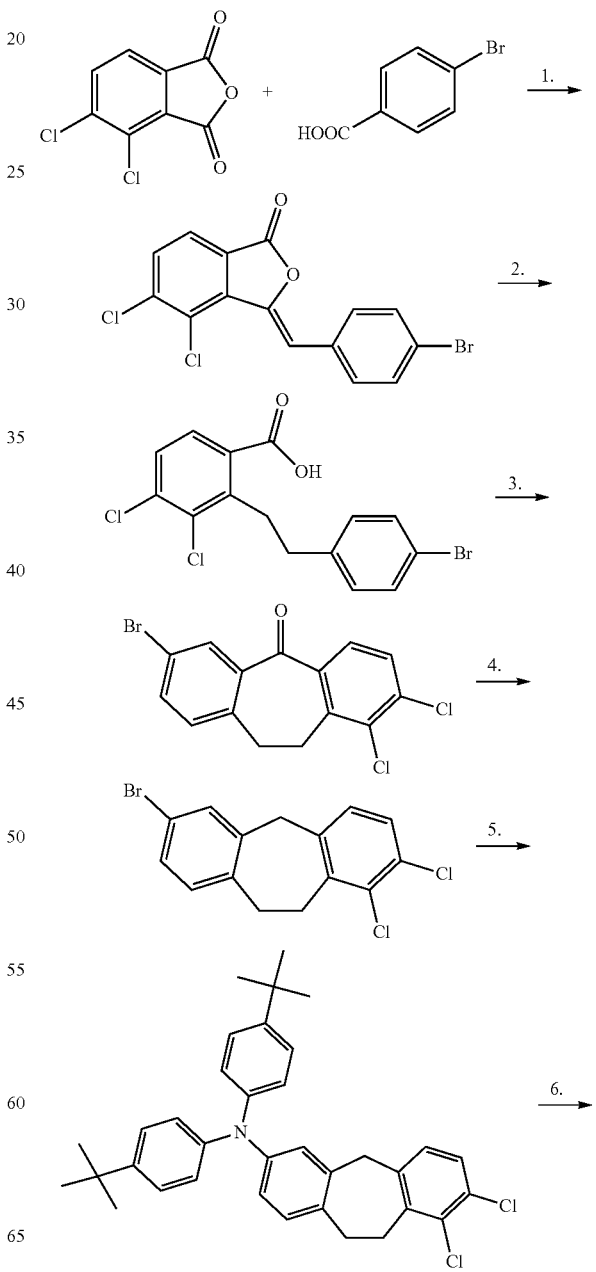

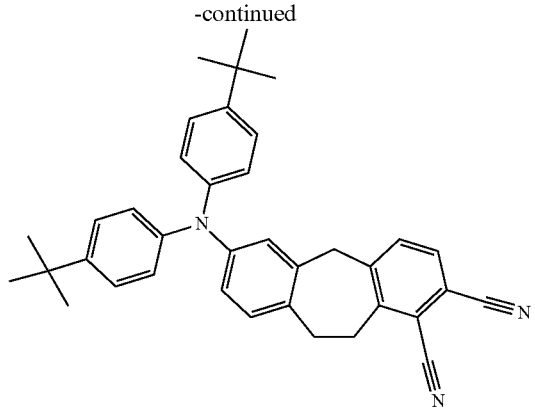

Reactants and reaction conditions (1) $CH_3CO_2Na$, 230° C., 3 hours
(2) $HPO_2$, $I_2$, red phosphorus, $CH_3COOH$, 80° C., 24 hours
(3) $(H_3PO_4)_n$, 175° C., 5 hours
(4) $Al[OCH(CH_3)_2]_3$, 275° C., 3 hours
(5) $(t-C_4H_9-C_6H_5)_2NH$, $Pd(CH_3COO)_2$, $P[(C(CH3)_3]_3$, $(CH_3)_3CONa$, 90° C., 19 hours
(6) $K_4[Fe(CN)_6]$, $Pd(CH_3COO)_2$, $P[(C(CH3)_3]_3$, $Na_2CO_3$, $(CH_3)_2NCHO$, 140° C., 12 hours Embodiment 5

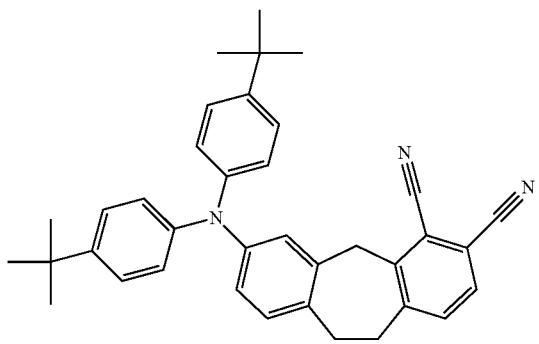 [SMILES: CC(C)(C)c1ccc(N(c2ccc(C(C)(C)C)cc2)c2ccc3c(c2)Cc2c(ccc(C#N)c2C#N)CC3)cc1]

Example Molecule 5

The example molecule 5 according to the invention would be detailed below. As shown from the frontier orbital in FIG. 13, the HOMO and LUMO were located in distinctly different spatial regions of the molecule. It was expected that the gap between the lowest triplet state and the singlet state above it was small enough that the molecule exhibited a significant TADF effect. The calculation of the example molecule 5 within the range of TD-DFT calculation (function B3LYP, basis set 6-31G (d, p)) showed that the energy level difference of the optimized triplet-state geometrical structure was $\Delta E(S_1-T_1)=150$ cm$^{-1}$. Therefore, the example molecule 5 was a good TADF emitter. The following reaction scheme illustrated the chemical synthesis of example molecule 5.

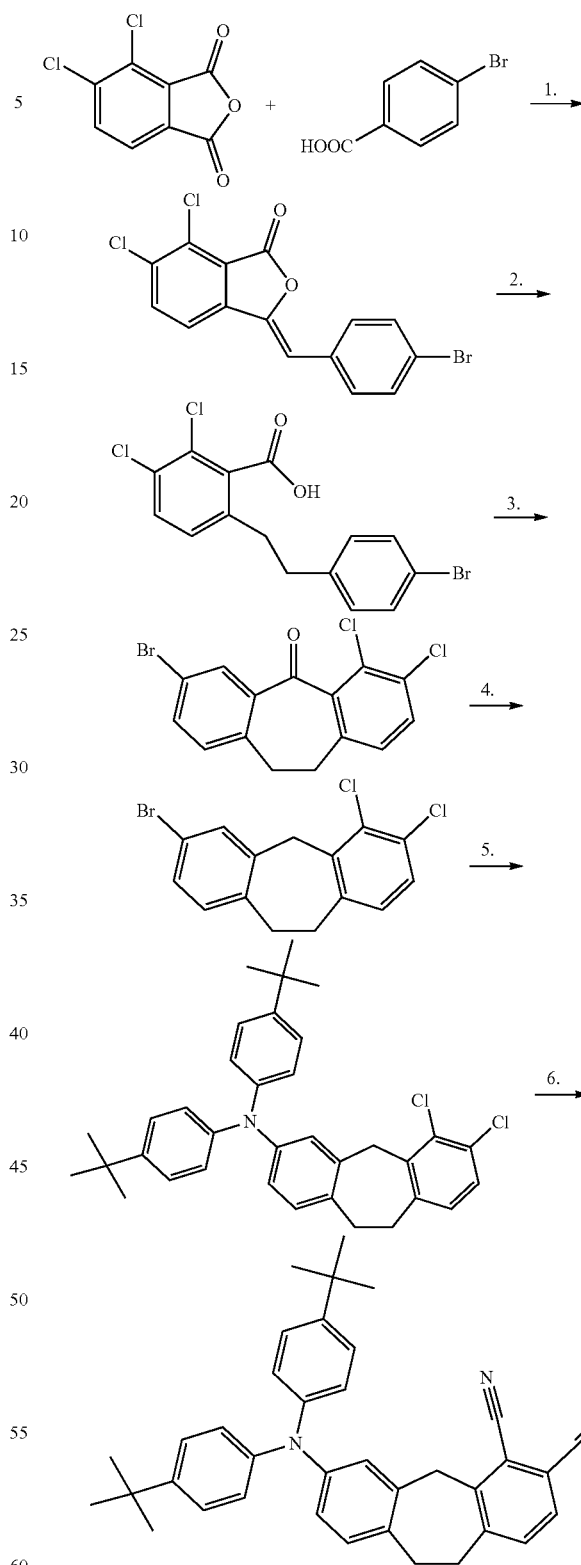

Reactants and reaction conditions:

(1) $CH_3CO_2Na$, 230° C., 3 hours
(2) $HPO_2$, $I_2$, red phosphorus, $CH_3COOH$, 80° C., 24 hours
(3) $(H_3PO_4)_n$, 175° C., 5 hours
(4) $Al[OCH(CH_3)_2]_3$, 275° C., 3 hours (5) (t-C$_4$H$_9$—C$_6$H$_5$)$_2$NH, Pd(CH$_3$COO)$_2$, P[(C(CH3)$_3$]$_3$, (CH$_3$)$_3$CONa, 90° C., 19 hours (6) K$_4$[Fe(CN)$_6$], Pd(CH$_3$COO)$_2$, P[(C(CH3)$_3$]$_3$, Na$_2$CO$_3$, (CH$_3$)$_2$NCHO, 140° C., 12 hours Embodiment 6

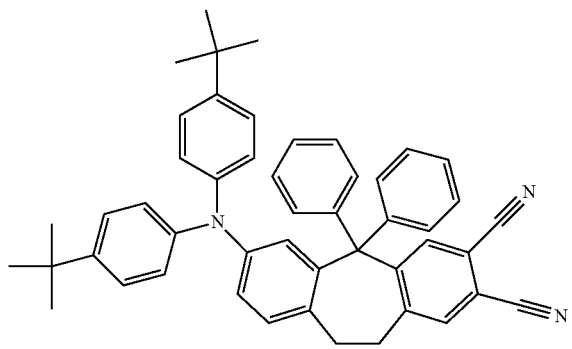 [SMILES: CC(C)(C)c1ccc(N(c2ccc(C(C)(C)C)cc2)c2ccc3c(c2)C(c2ccccc2)(c2ccccc2)c2cc(C#N)c(C#N)cc2CC3)cc1]

Example Molecule 6

The example molecule 6 according to the invention would be detailed below. As shown from the frontier orbital in FIG. 14, the HOMO and LUMO were located in distinctly different spatial regions of the molecule. It was expected that the gap between the lowest triplet state and the singlet state above it was small enough that the molecule exhibited a significant TADF effect. The calculation of the example molecule 6 within the range of TD-DFT calculation (function B3LYP, basis set 6-31G (d, p)) showed that the energy level difference of the optimized triplet-state geometrical structure was $\Delta E(S_1-T_1)=30$ cm$^{-1}$. Therefore, the example molecule 6 was a good TADF emitter.

Embodiment 7

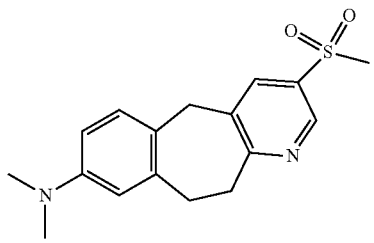

Example Molecule 7

FIG. 15 showed the frontier orbitals HOMO and LUMO of example molecule 7. Since these orbitals were located in distinctly different spatial regions of the molecule, it could be expected that the gap between the lowest triplet state and the singlet state above it was small enough that the molecule exhibited a significant TADF effect. The calculation of the example molecule 7 within the range of TD-DFT calculation (function B3LYP, basis set 6-31G (d, p)) showed that the energy level difference of the optimized triplet-state geometrical structure was $\Delta E(S_1-T_1)=550$ cm$^{-1}$. Therefore, the example molecule 7 was a good TADF emitter.

The following reaction scheme illustrated the chemical synthesis of example molecule 7.

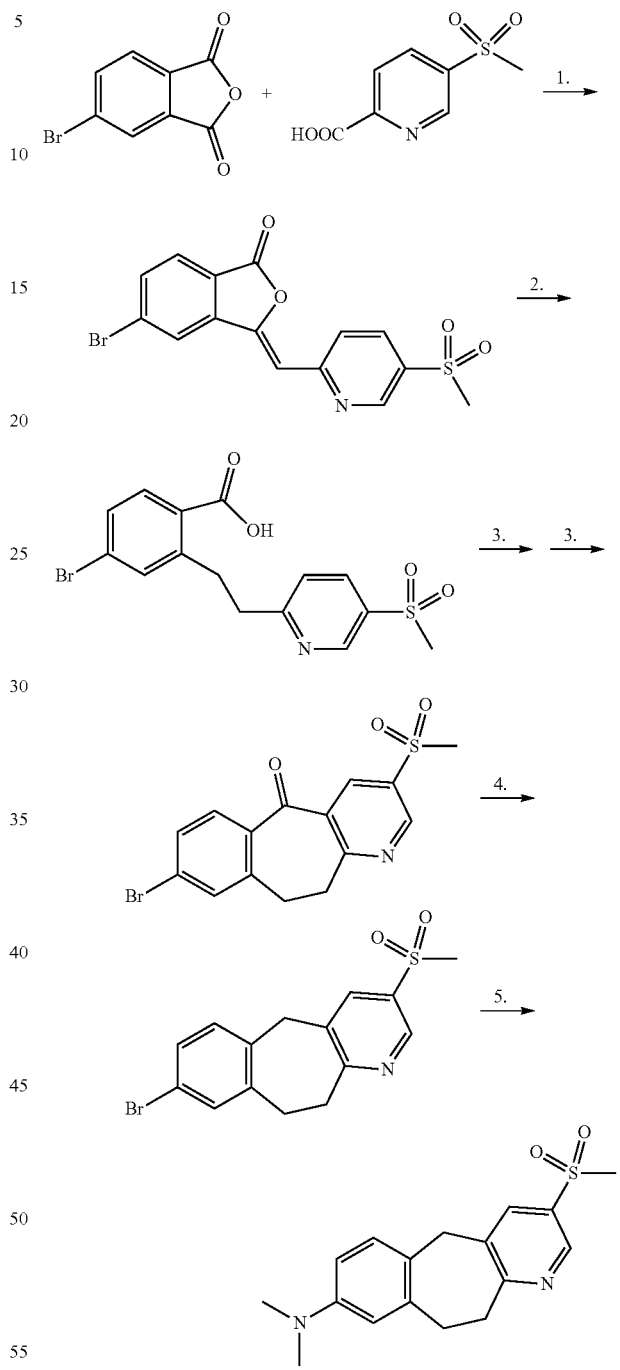

Reactants and reaction conditions:

(1) CH$_3$CO$_2$Na, 230° C., 3 hours (2) HI (57% aqueous solution), red phosphorus, 80° C., 24 hours (3) (H$_3$PO$_4$)$_n$, 175° C., 5 hours (4) Al[OCH(CH$_3$)$_2$]$_3$, 275° C., 3 hours (5) (CH$_3$)$_2$NH, Pd (CH$_3$COO)$_2$, P[(C(CH$_3$)$_3$]$_3$, (CH$_3$)$_3$CONa, 90° C., 19 hours

Embodiment 8

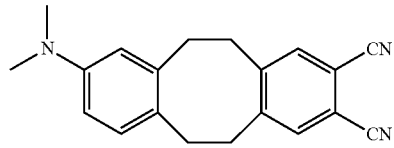 [SMILES: CN(C)c1ccc2c(c1)CCc1cc(C#N)c(C#N)cc1CC2]

Example Molecule 8

As shown from the frontier orbitals in FIG. 16, the HOMO and LUMO were located in distinctly different spatial regions of the molecule. It was expected that the gap between the lowest triplet state and the singlet state above it was small enough that the molecule exhibited a significant TADF effect. The calculation of the example molecule 8 within the range of TD-DFT calculation (function B3LYP, basis set 6-31G (d, p)) showed that the energy level difference of the optimized triplet-state geometrical structure was $\Delta E(S_1-T_1)=540$ cm$^{-1}$. Therefore, the example molecule 8 was a good TADF emitter.

The following reaction scheme illustrated the chemical synthesis of example molecule 8.

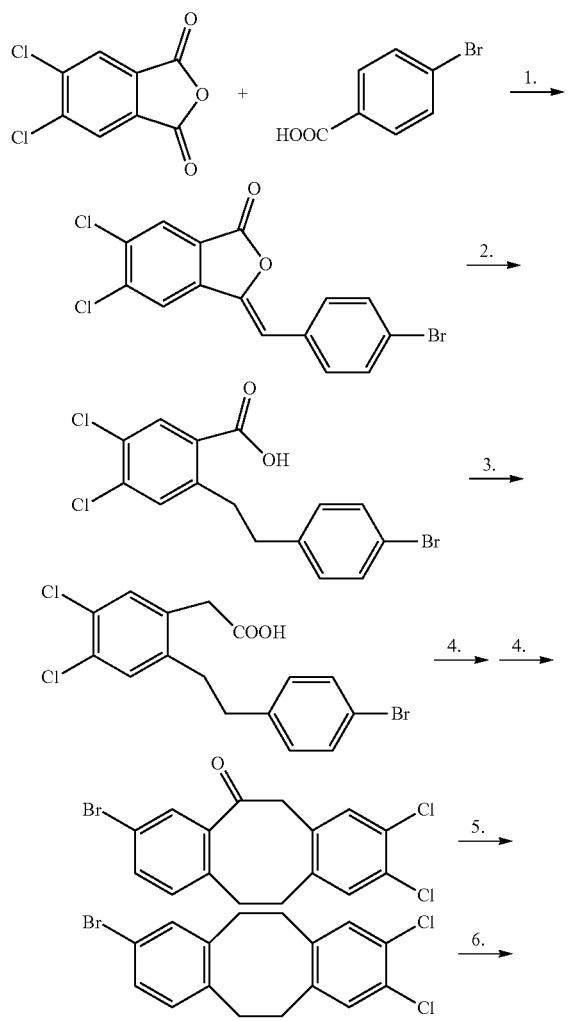

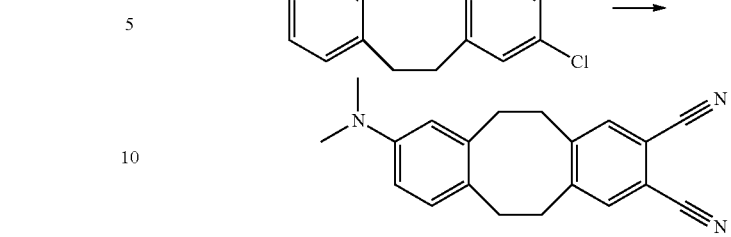

Reactants and reaction conditions:
(1) $CH_3CO_2Na$, 230° C., 3 hours
(2) HI (57% aqueous solution), red phosphorus, 80° C., 24 hours
(3) $CH_2N_2$, $SO_2Cl_2$, 80° C., 2 hours; $(CH_3)_3COH$, $C_6H_5COOAg$, $Et_3N$, 90° C., 2 hours
(4) $(H_3PO_4)_n$, 175° C., 5 hours
(5) $Al[OCH(CH_3)_2]_3$, 275° C., 3 hours
(6) $(CH_3)_2NH$, $Pd(CH_3COO)_2$, $P[(C(CH3)_3]_3$, $(CH_3)_3CONa$, 90° C., 19 hours
(7) $K_4[Fe(CN)_6]$, $Pd(CH_3COO)_2$, $P[(C(CH3)_3]_3$, $Na_2CO_3$, $(CH_3)_2NCHO$, 140° C., 12 hours

Embodiment 9

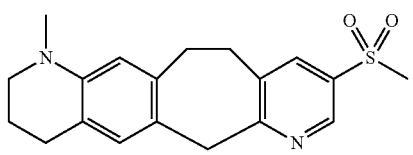 [SMILES: CN1CCCc2cc3c(cc21)CCc1cc(S(C)(=O)=O)cnc1C3]

Example Molecule 9

FIG. 17 showed the frontier orbitals HOMO and LUMO of example molecule 9. Since these orbitals were located in distinctly different spatial regions of the molecule, it could be expected that the gap between the lowest triplet state and the singlet state above it was small enough that the molecule exhibited a significant TADF effect. The calculation of the example molecule 9 within the range of TD-DFT calculation (function B3LYP, basis set 6-31G (d, p)) showed that the energy level difference of the optimized triplet-state geometrical structure was $\Delta E(S_1-T_1)=550$ cm$^{-1}$. Therefore, the example molecule 9 was a good TADF emitter.

Embodiment 10

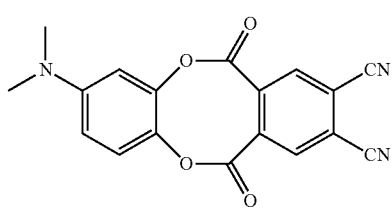 [SMILES: CN(C)c1ccc2c(c1)OC(=O)c1cc(C#N)c(C#N)cc1C(=O)O2]

Example Molecule 10

FIG. 18 showed the frontier orbitals HOMO and LUMO of example molecule 10. Since these orbitals were located in distinctly different spatial regions of the molecule, it could be expected that the gap between the lowest triplet state and the singlet state above it was small enough that the molecule exhibited a significant TADF effect. The calculation of the example molecule 10 within the range of TD-DFT calculation (function B3LYP, basis set 6-31G (d, p)) showed that the energy level difference of the optimized triplet-state geometrical structure was $\Delta E(S_1-T_1)=140$ cm$^{-1}$. Therefore, the example molecule 10 was a good TADF emitter.

Embodiment 11

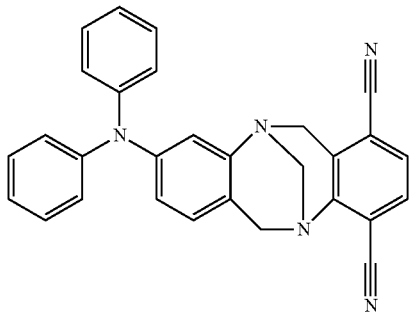 [SMILES: N#Cc1ccc(C#N)c2c1CN1CN2Cc2ccc(N(c3ccccc3)c3ccccc3)cc21]

Example Molecule 11

FIG. 19 showed the frontier orbitals HOMO and LUMO of example molecule 11. Since these orbitals were located in distinctly different spatial regions of the molecule, it could be expected that the gap between the lowest triplet state and the singlet state above it was small enough that the molecule exhibited a significant TADF effect. The calculation of the example molecule 11 within the range of TD-DFT calculation (function B3LYP, basis set 6-31G (d, p)) showed that the energy level difference of the optimized triplet-state geometrical structure was $\Delta E(S_1-T_1)=420$ cm$^{-1}$. Therefore, the example molecule 11 was a good TADF emitter.

Embodiment 12

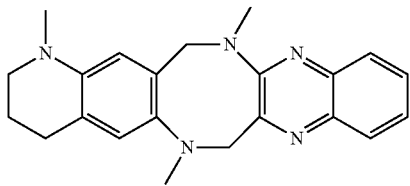 [SMILES: CN1CCCc2cc3c(cc21)CN(C)c1nc2ccccc2nc1CN3C]

Example Molecule 12

FIG. 20 showed the frontier orbitals HOMO and LUMO of example molecule 12. Since these orbitals were located in distinctly different spatial regions of the molecule, it could be expected that the gap between the lowest triplet state and the singlet state above it was small enough that the molecule exhibited a significant TADF effect. The calculation of the example molecule 12 within the range of TD-DFT calculation (function B3LYP, basis set 6-31G (d, p)) showed that the energy level difference of the optimized triplet-state geometrical structure was $\Delta E(S_1-T_1)=1250$ cm$^{-1}$. Therefore, the example molecule 12 was a good TADF emitter.

FIG. 21 showed other example molecules.

long time spectrum (TADF2) with time delay t=5 μs (time window Δt=30 μs). Excitation: Short-time spectrum: 375 nm, pulse width 70 ps, long-time spectrum, excitation: 355 nm, pulse width: 2.9 ns.

Figure 1:
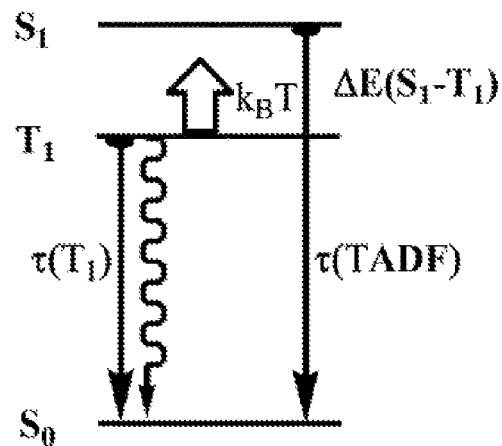
FIG. 1 shows a schematic diagram of the energy level of the thermally activated delayed fluorescence (TADF) process. $k_BT$ represents thermal energy with a Boltzmann constant $k_B$ and an absolute temperature T. This figure shows both the radiative and non-radiative (marked by wavy lines) attenuation processes of the radiation TADF process and the low-temperature observable $T_1$ state. The figure does not mark the spontaneous $S_1 \rightarrow S_0$ fluorescence process.
Figure 2:
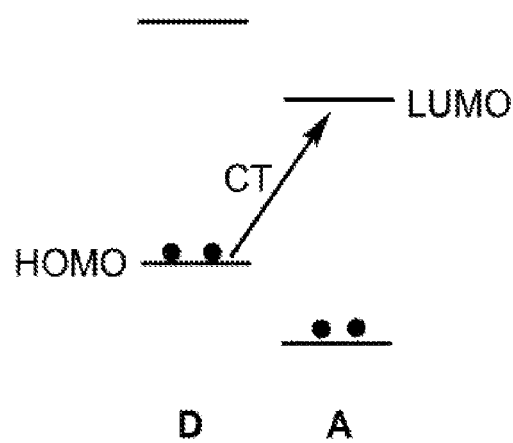
FIG. 2 shows a schematic diagram of orbital energies of molecules with donor fragments and receptor fragments (D-A molecules) according to the present invention. Due to non-conjugated bridges, the interaction between the donor and acceptor tracks is small. Thus, the electronic properties of the D and A fragments can be approximated separately, that is, the D orbital energy is approximately equal to the energy of the corresponding free (unlinked) donor molecule, and the A orbital energy is approximately equal to the energy of the corresponding free (unlinked) acceptor molecule. The HOMO energy of the isolated donor (electron-rich) is significantly higher than HOMO energy of the isolated acceptor (electron-deficient). The LUMO of an isolated donor is much higher than the LUMO energy of an acceptor. Therefore, the HOMO of the D-A molecule is mainly located on the D fragment, while the LUMO of the D-A molecule is mainly located on the A fragment.
Figure 3:
FIG. 3 shows an isosurface of the frontier orbital of the example molecule 1 (see Embodiment 1), HOMO: left, LUMO: right. The electronic ground state $S_0$ geometry is optimized. Calculation method: DFT and TD-DFT, function: B3LYP, basis set: 6-31G (d, p), calculation software: Gaussian 09. The calculation result showed that the energy difference between the singlet state-CT state and the triplet state-CT state is 75 cm$^{-1}$ ($S_0$-geometry). This value indicates that the example molecule 1 is a good TADF emitter.
Figure 4:
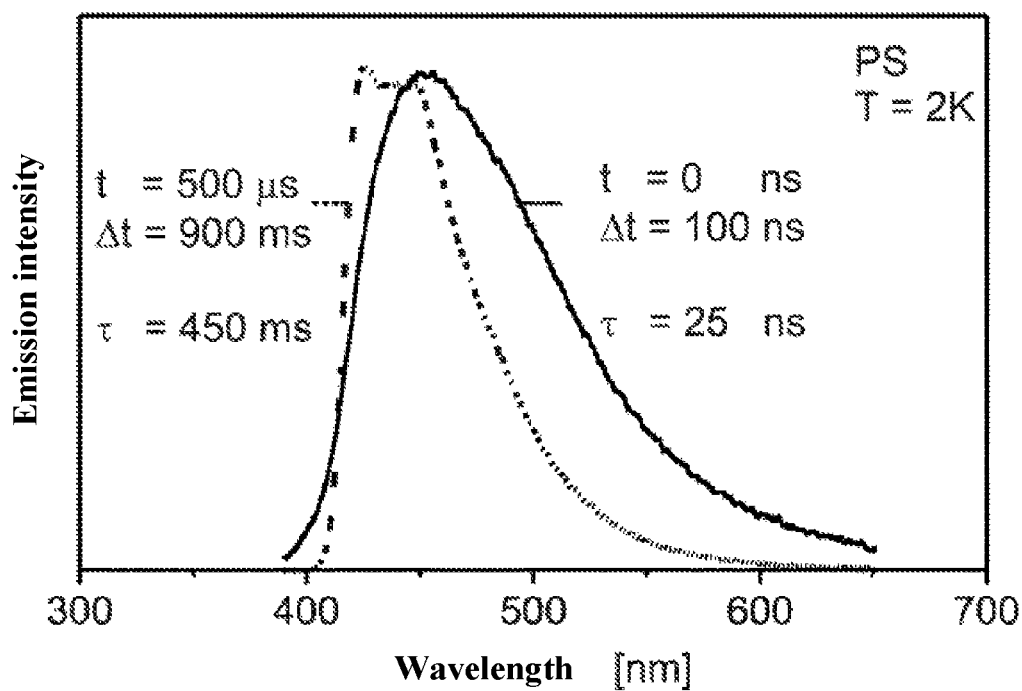
FIG. 4 shows time-resolved emission spectra of example molecule 1 doped about 1% by weight in PS at T=2K. Record the short-term spectrum in case of no time delay (t=0 ns) and detection time window $\Delta1$ t=100 ns and record the long-term spectrum in case of a time delay t=500 μs (time window $\Delta t$=900 ms). Excitation: short-time spectrum: 375 nm, pulse width 70 ps; long-time spectrum, excitation: 365 nm, pulse width: 10 ns.
Figure 5:
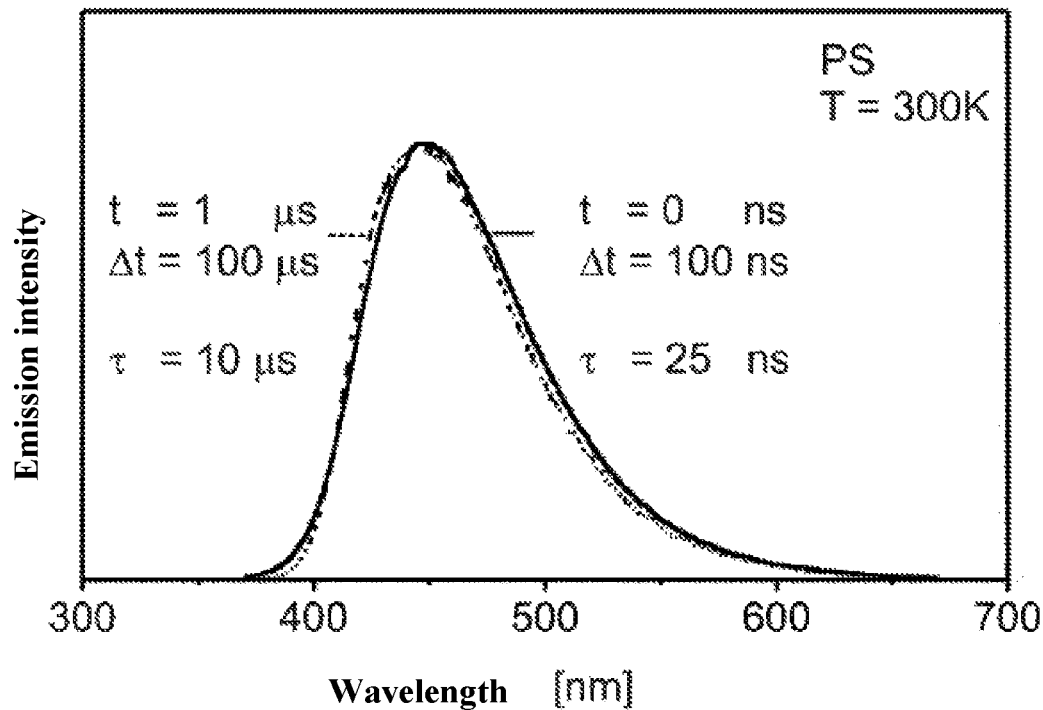
FIG. 5 shows time-resolved emission spectra and decay time τ of example molecule 1 doped about 1% by weight in PS at T=300K. Record the short-term spectrum in case of no time delay (t=0 ns) and detection time window $\Delta t$=100 ns and record the long-term spectrum in case of a time delay t=1 μs (time window $\Delta t$=100 μs). Excitation: short-time spectrum: 375 nm, pulse width 70 ps; long-time spectrum, excitation: 355 nm, pulse width: 2.9 ns.
Figure 6:
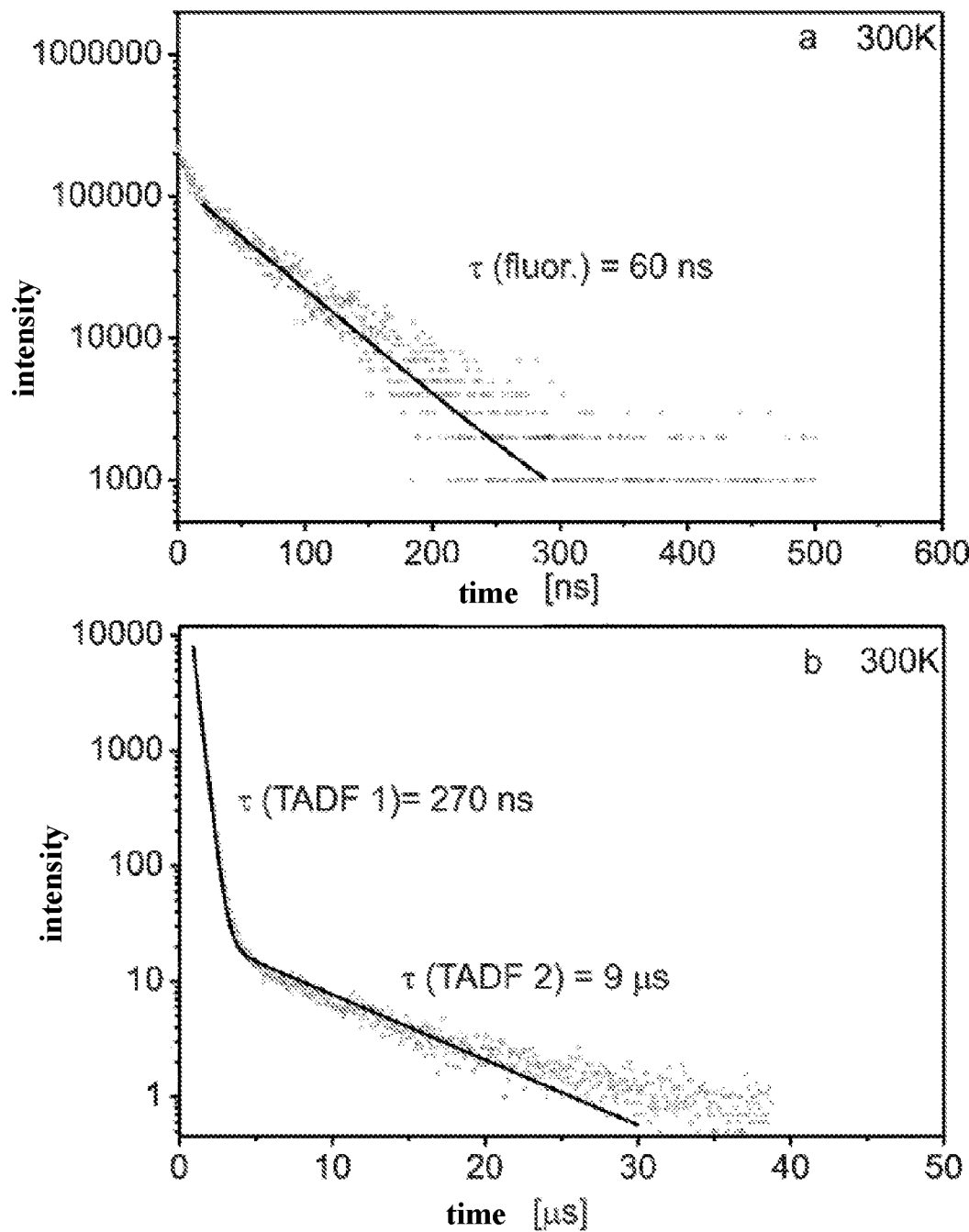
FIG. 6 shows the emission decay behaviors of example substance 1 dissolved in toluene, (a) short time domain (spontaneous fluorescence) and (b) long time domain, T=300K. Record the spontaneous fluorescence emission decay time τ(fluorescence)=60n and TADF decay time τ(TADF 1)=270 ns and τ(TADF 2)=9 μs of respective components. Introduce nitrogen for 120 min to degas the solution. Excitation wavelength: 355 nm, pulse duration: 2.9 ns, and concentration: about 10$^{-5}$ mol/l.
Figure 7:
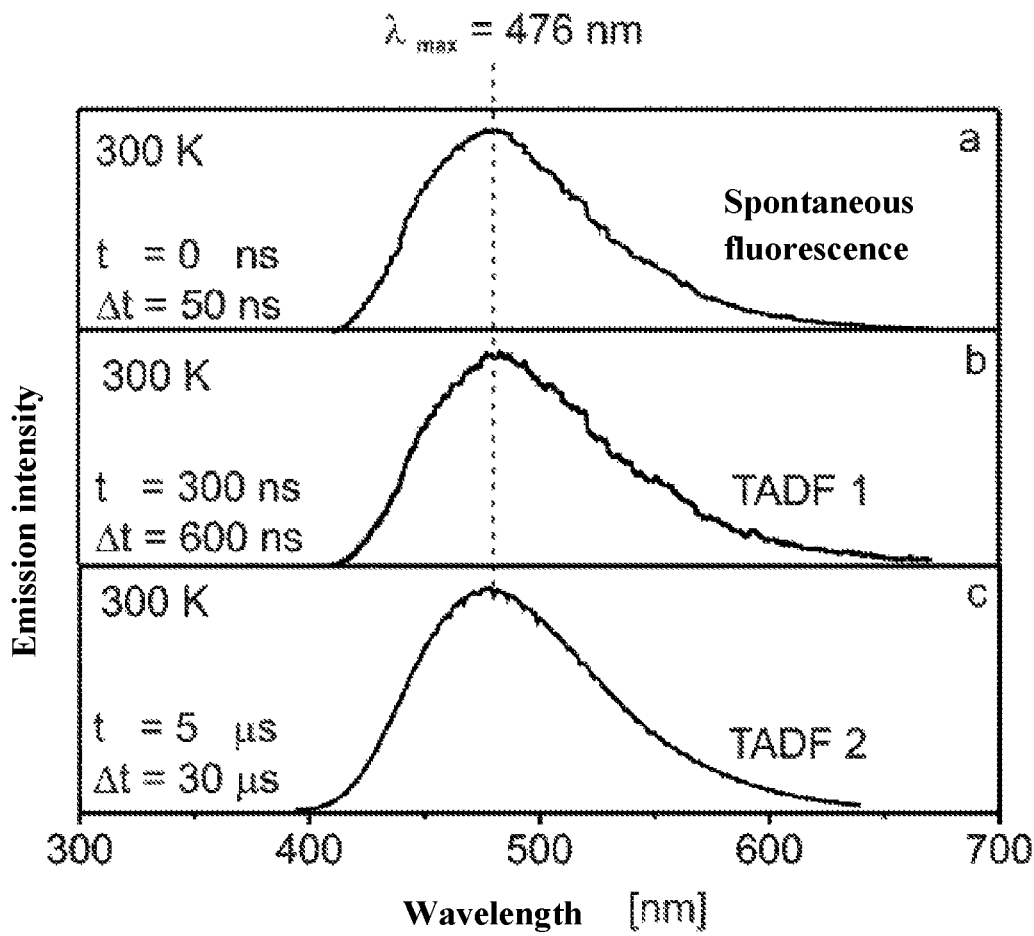
FIG. 7 shows the time-resolved emission spectra of example molecule 1 at a concentration of 10$^{-5}$ M dissolved in toluene when T=300K. Record (a) short-time spectra (spontaneous fluorescence) of no time delay (t=0 ns) and test time window $\Delta t$=50 ns, (b) long-term spectrum (TADF1) with time delay t=300 μs (time window $\Delta t$=600 ns) and (c)
Figure 8:
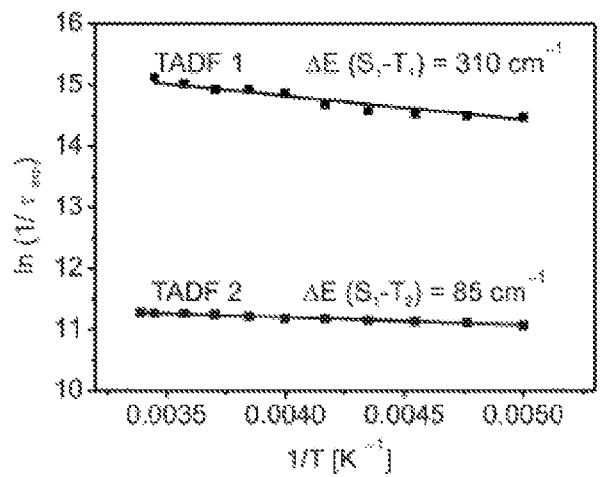

FIG. 8 shows the Boltzmann diagram (Arrhenius diagram) of long-lived composition of the corresponding emission decay time of example molecule 1 dissolved in toluene according to equation 3. The activation energy $\Delta E(S_1-T_1)=(310\pm10)$cm-$^1$ and $\Delta E(S_1-T_2)=(85\pm5)$cm$^{-1}$ obtained by fitting. The T1 state is the local state, and the T2 is classified as the charge donor transfer state.

Figure 9:
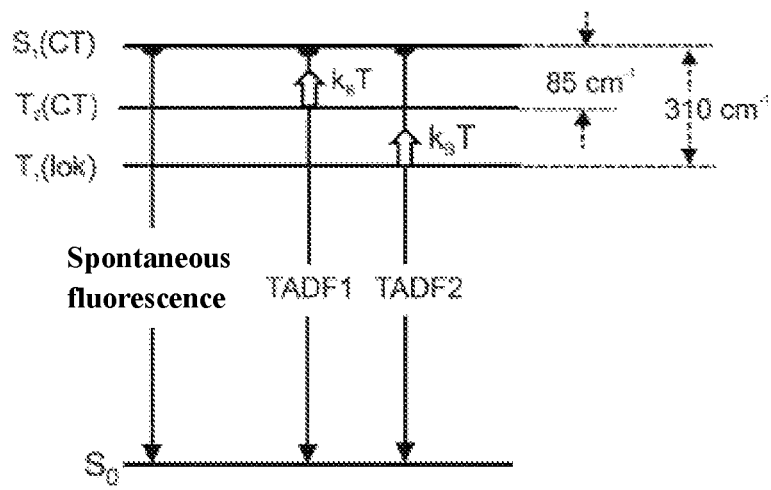

FIG. 9 shows the formal energy level diagram, used to schematically describe the experimental emission decay time and activation energy. $T_1$(lok) represents the local state, while $T_2$(CT) and $S_1$(CT) represent the charge transfer state. The heat returns from $T_1$(lok) and $T_2$(CT) to the $S_1$(CT) state, resulting in two TADF processes.

Figure 10:
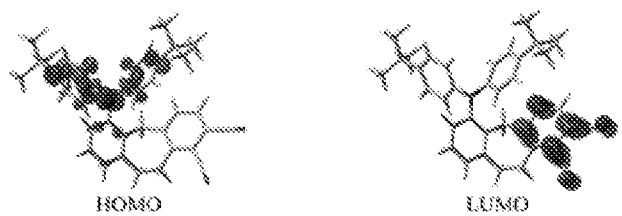

FIG. 10 shows an isosurface of the frontier orbital of the example molecule 2 (see Embodiment 2), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=85$ cm-$^1$ Both values indicate that example molecule 2 is a good TADF emitter.

Figure 11:
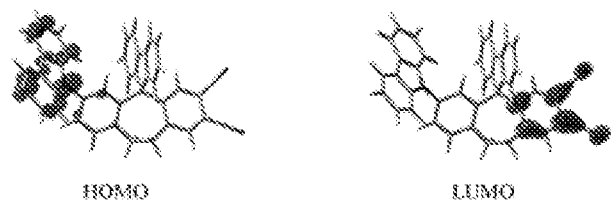

FIG. 11 shows an isosurface of the frontier orbital of the example molecule 3 (see Embodiment 3), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=55$ cm-$^1$ The result indicates that example molecule 3 is a good TADF emitter.

Figure 12:
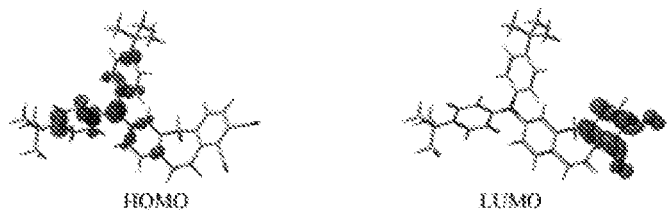

FIG. 12 shows an isosurface of the frontier orbital of the example molecule 4 (see Embodiment 4), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=88$ cm-$^1$ The result indicates that example molecule 4 is a good TADF emitter.

Figure 13:
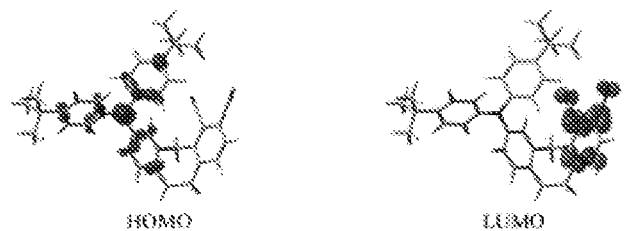

FIG. 13 shows an isosurface of the frontier orbital of the example molecule 5 (see Embodiment 5), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=150$ cm-$^1$ The result indicates that example molecule 5 is a good TADF emitter.

Figure 14:
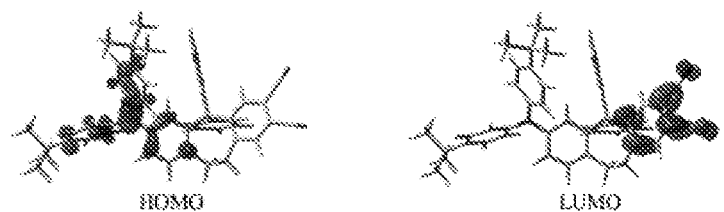

FIG. 14 shows an isosurface of the frontier orbital of the example molecule 6 (see Embodiment 6), HOMO: left, LUMO: right. Optimization of the electron ground state $S_0$ and the lowest triplet state $T_1$ geometry. Calculation method: DFT and TD-DFT, function: B3LYP, basis set: 6-31G (d, p), calculation software: Gaussian 09. The result: $\Delta E(S_1-T_1)=35$ cm-$^1$ ($S_0$-geometry) and 30 cm$^{-1}$ ($T_1$-geometry). Both values indicate that example molecule 2 is a good TADF emitter.

Figure 15:
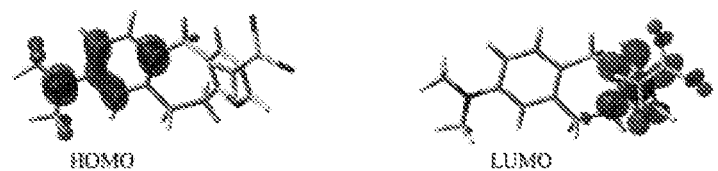

FIG. 15 shows an isosurface of the frontier orbital of the example molecule 7 (see Embodiment 7), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=550$ cm-$^1$ The result indicates that example molecule 7 is a good TADF emitter.

Figure 16:
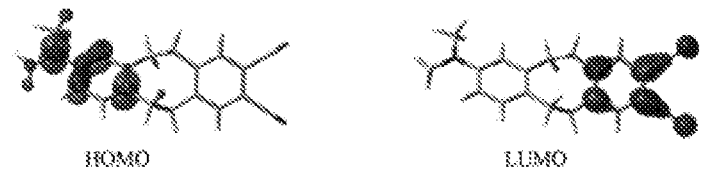

FIG. 16 shows an isosurface of the frontier orbital of the example molecule 8 (see Embodiment 8), HOMO: left, LUMO: right. Optimization of the lowest triplet state T, geometry. Calculation method: DFT and TD-DFT, function: B3LYP, basis set: 6-31G (d, p), calculation software: Gaussian 09. The result: $\Delta E(S_1-T_1)=540$ cm-$^1$ (T, geometry) The result indicates that example molecule 8 is a good TADF emitter.

Figure 17:
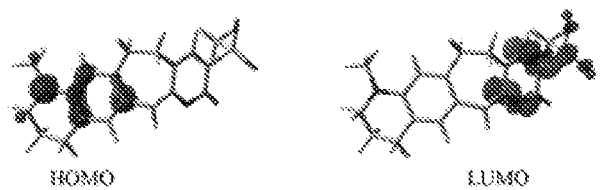

FIG. 17 shows an isosurface of the frontier orbital of the example molecule 9 (see Embodiment 9), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=550$ cm$^{-1}$ ($T_1$-geometry) The result indicates that example molecule 9 is a good TADF emitter.

Figure 18:
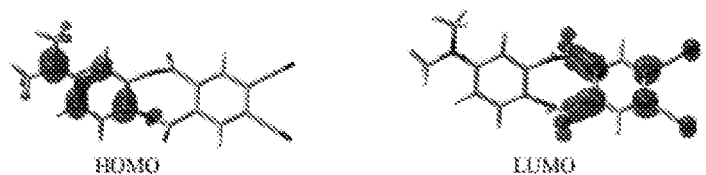

FIG. 18 shows an isosurface of the frontier orbital of the example molecule 10 (see Embodiment 10), HOMO: left, LUMO: right. Optimization of the electron ground state geometry. Calculation method: DFT and TD-DFT, function: B3LYP, basis set: 6-31G (d, p), calculation software: Gaussian 09. The result: $\Delta E(S_1-T_1)=140$ cm-$^1$ The result indicates that example molecule 10 is a good TADF emitter.

Figure 19:
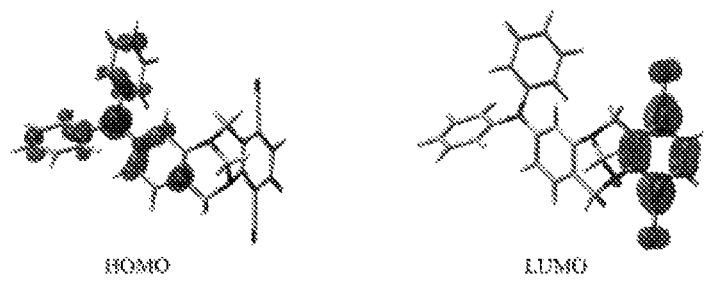

FIG. 19 shows an isosurface of the frontier orbital of the example molecule 11 (see Embodiment 11), HOMO: left, LUMO: right. Optimization of the electron $T_1$ state geometry. Calculation method: DFT and TD-DFT, function: B3LYP, basis set: 6-31G (d, p), calculation software: Gaussian 09. The result: $\Delta E(S_1-T_1)=420$ cm$^{-1}$ The result indicates that example molecule 11 is a good TADF emitter.

Figure 20:
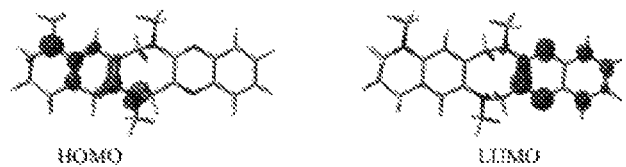

FIG. 20 shows an isosurface of the frontier orbital of the example molecule 12 (see Embodiment 12), HOMO: left, LUMO: right. Optimization of the lowest triplet state $T_1$ geometry. Calculation method: DFT and TD-DFT, function: B3LYP, basis set: 6-31G (d, p), calculation software: Gaussian 09. The result: $\Delta E(S_1-T_1)=1250$ cm-$^1$ ($T_1$ geometry) The result indicates that example molecule 12 is a good TADF emitter.

Figure 21A:
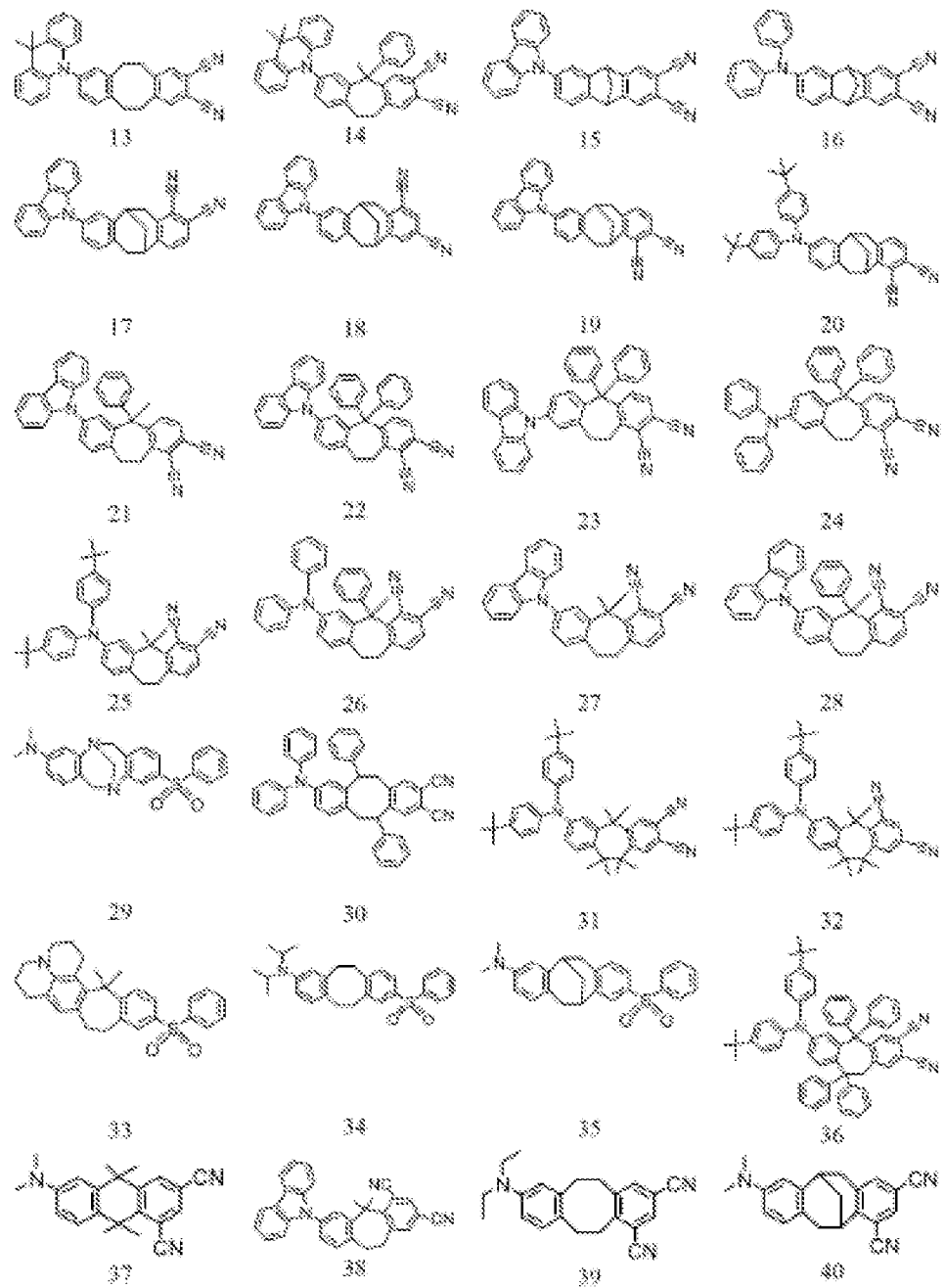
Figure 21B:
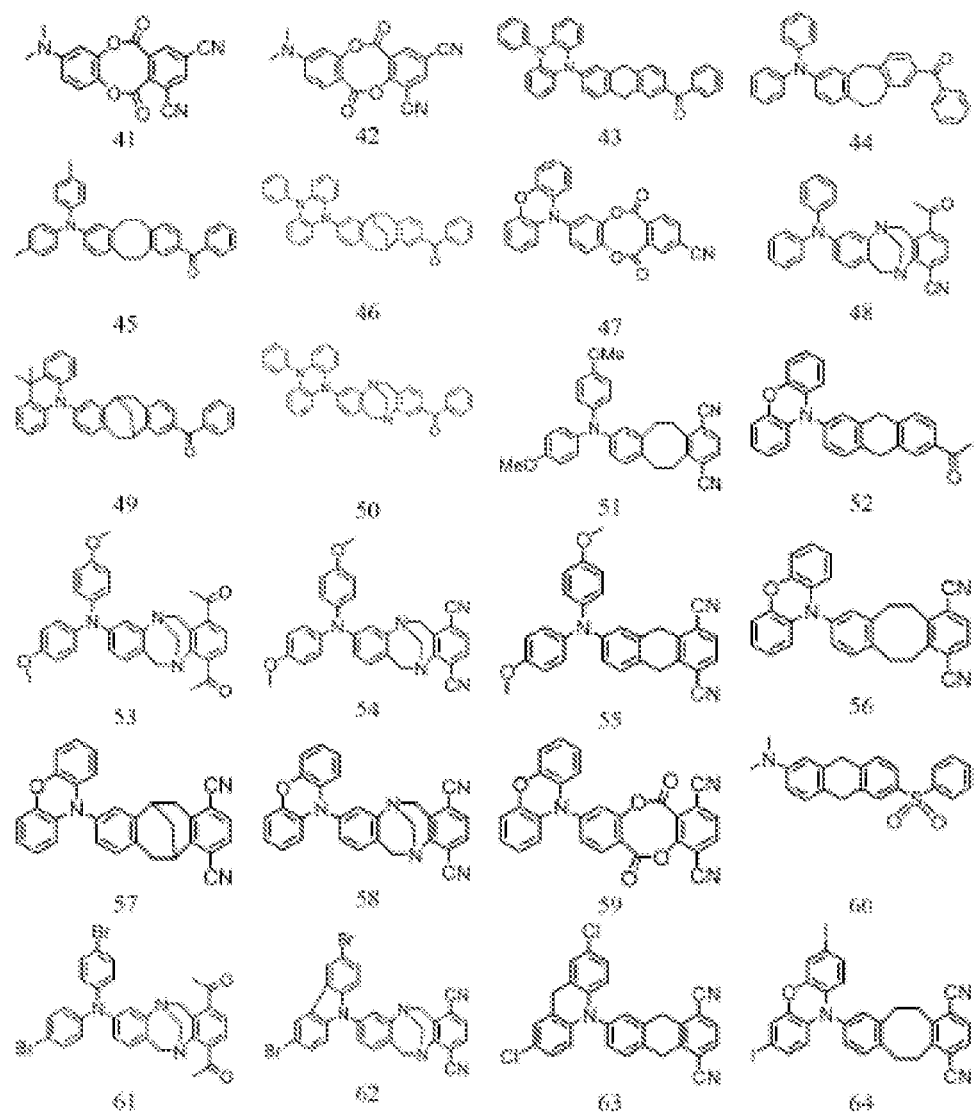

FIG. 21 A and B show schematic representations of other molecules according to the invention.

What is claimed is:
1. An organic molecule for luminescence, comprising the structure according to Formula XVIII or Formula XIX,

Formula XVIII

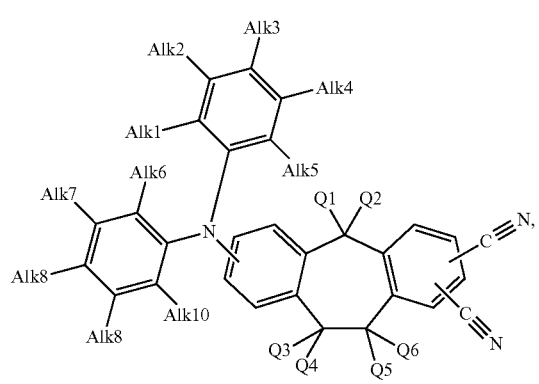

-continued

Formula XIX

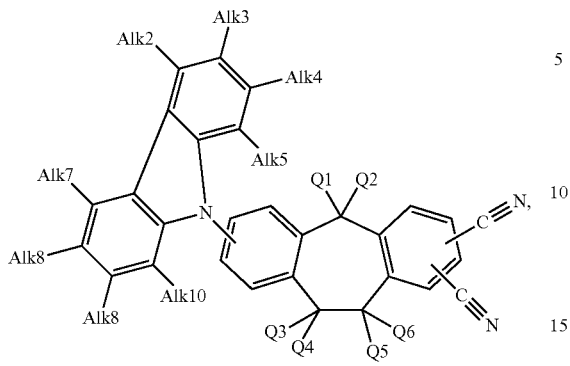

wherein Q3, Q4, Q5, and Q6 are each independently selected from the group consisting of H, $CH_3$, $C_2H_5$, $C_3H_7$, $C_4H_9$, $C_5H_{11}$, $C_6H_{13}$, phenyl, tolyl, xylyl, benzyl, thienyl, pyrazolyl, diazolyl, triazolyl, tetrazolyl, oxazolyl, oxadiazolyl, furyl, and carbazolyl;

Q1 and Q2 are each independently selected from the group consisting of H, $CH_3$, $C_2H_5$, $C_3H_7$, $C_4H_9$, $C_5H_{11}$, $C_6H_{13}$, tolyl, xylyl, benzyl, thienyl, pyrazolyl, diazolyl, triazolyl, tetrazolyl, oxazolyl, oxadiazolyl, furyl, and carbazolyl;

Q1 and Q2, Q3 and Q4, and Q5 and Q6 are optionally linked, thereby forming a cycloalkyl system or an aromatic spirocyclic system; and Alk2, Alk3, Alk4, Alk5, Alk7, Alk8, Alk9, and Alk10 are, independently of each other, H or an unbranched or branched aliphatic group or a cycloalkyl group Wherein at least one of Q3-Q6 is not hydrogen.

2. An organic molecule for luminescence, comprising the structure of Formula I,

Formula I

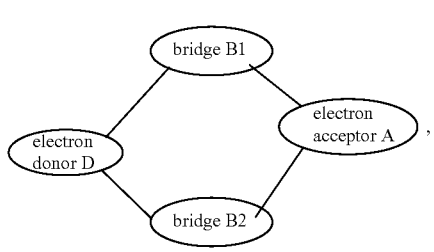

where each of the electron acceptor A and the electron donor D independently is an aromatic or heteroaromatic group that optionally has at least one substitution, the bridge B1 and the bridge B2 connect organic groups of the electron donor D and the electron acceptor A in a non-conjugated manner, the bridge B1 and the bridge B2 are each independently represented by the structure of Formula V,

A2-A3 #     Formula V where # represents a linking site of the bridge B2 for connecting to the electron donor D or the electron acceptor A;

A2 is selected from the group consisting of

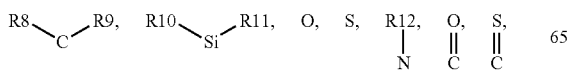

-continued

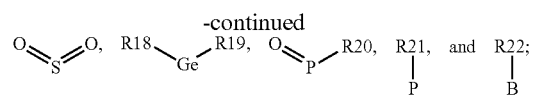

A3 is selected from the group consisting of

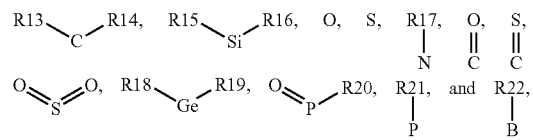

each of R8 to R17 is independently selected from the group consisting of —H, substituted or unsubstituted alkyl, cycloalkyl, substituted or unsubstituted alkenyl, substituted or unsubstituted alkynyl, substituted or unsubstituted aryl, substituted or unsubstituted heteroaryl, alkoxy (—OR'), thioalkyl (—SR'), sulfonyl (—SO2R'), acyl (—COR'), formyl (—CHO), carboxyl (—CO$_2$R'), boryl (—BR'R''), sulfinyl (—SOR'), amine (—NR'R''), phosphino (—PR'R''), phosphinyl (—POR'R''), amido (—NR'COR''), silyl (—SiR'R''R'''), cyano (—CN), nitro (—NO$_2$), nitroso (—NO), isocyanato (—NCO), thiocyano (—NCS), and halogen, where R', R'', and R''' each have the same definition as R8 to R17;

at least one of R8, R9, R13, and R14 is the substituted or unsubstituted alkyl, the cycloalkyl, the substituted or unsubstituted alkenyl, the substituted or unsubstituted alkynyl, the substituted or unsubstituted aryl, the substituted or unsubstituted heteroaryl, the alkoxy, the thioalkyl, the sulfonyl, the acyl, the formyl, the carboxyl, the boryl, the sulfinyl, the amine, the phosphino, the phosphinyl, the amido, the silyl, cyano (—CN), nitro (—NO$_2$), nitroso (—NO), isocyanato (—NCO), thiocyano (—NCS), or halogen;

each of R18 to R22 is independently selected from the group consisting of —H, substituted or unsubstituted alkyl, cycloalkyl, substituted or unsubstituted alkenyl, substituted or unsubstituted alkynyl, substituted or unsubstituted aryl, substituted or unsubstituted heteroaryl, alkoxy (—OR'), thioalkyl (—SR'), sulfonyl (—SO$_2$R'), acyl (—COR'), formyl (—CHO), carboxyl (—CO$_2$R), boryl (—BR'R''), sulfinyl (—SOR'), amine (—NR'R''), phosphino (—PR'R''), phosphinyl (—POR'R''), amido (—NR'COR''), silyl (—SiR'R''R'''), cyano (—CN), nitro (—NO$_2$), nitroso (—NO), isocyanato (—NCO), thiocyano (—NCS), and halogen, where R', R'', and R''' each have the same definition as R8;

the halogen is selected from the group consisting of —F, —Cl, —Br, and —I, the electron donor D and the electron acceptor A each independently include an aromatic or heteroaromatic group represented by Formula II or Formula III, Formula II

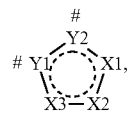

Formula III

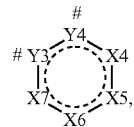

wherein the electron donor D and the electron acceptor A are different from each other, Formula II and Formula III are optionally part of a fused ring system, and Formula II and Formula III have # positions, the electron donor D and the electron acceptor A are linked to the bridge B1 and bridge B2 via the # positions, Y1, Y2, Y3, and Y4 are independently selected from the group consisting of C and N, each of X4 to X7 is independently selected from the group consisting of N, CH, NH, and C-R1, and at least one of X4 to X7 is C-R1, each of X1 to X3 is independently selected from the group consisting of N, O, S, Se, CH, NH, and C-R1, and at least one of X1 to X3 is C-R1, wherein R1 is independently selected from the group consisting of —H, substituted or unsubstituted alkyl, cycloalkyl, substituted or unsubstituted alkenyl, substituted or unsubstituted alkynyl, substituted or unsubstituted aryl, substituted or unsubstituted heteroaryl, alkoxy (—OR'), thioalkyl (—SR'), sulfonyl (—SO₂R'), acyl (—COR'), formyl (—CHO), carboxyl (—CO₂R'), boryl (—BR'R''), sulfinyl (—SOR'), amine (—NR'R''), phosphino (—PR'R''), phosphinyl (—POR'R''), amido (—NR'COR''), silyl (—SiR'R''R'''), cyano (—CN), nitro (—NO₂), nitroso (—NO), isocyanato (—NCO), and thiocyano (—NCS), wherein R', R'', and R''' each have the same definition as R1, and R', R'', and R''' are optionally linked to each other to form an additional aliphatic, aromatic or heteroaromatic ring system, the alkyl is selected from the group consisting of methyl, ethyl, n-propyl, isopropyl, n-butyl, isobutyl, tert-butyl, and adamantyl, the cycloalkyl is selected from the group consisting of cyclopropyl, cyclopentyl, cyclohexyl, the alkenyl is vinyl or allyl, the alkynyl is ethynyl, and the heteroaryl is selected from the group consisting of furyl, thienyl, and pyrrolyl, and the energy difference ΔE(S1-T1) between the lowest excited singlet (S1) state of the organic molecule and the triplet (T1) state of the organic molecule is less than 2000 cm⁻¹.

3. An organic molecule for luminescence, comprising the structure of Formula I,

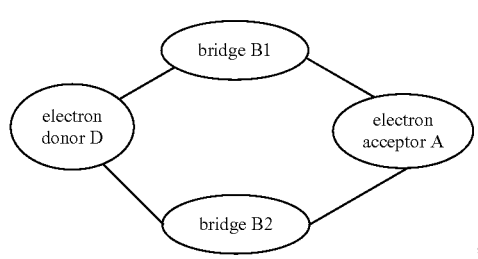

Formula I where each of the electron acceptor A and the electron donor D independently is an aromatic or heteroaromatic group that optionally has at least one substitution, the bridge B1 and the bridge B2 connect organic groups of the electron donor D and the electron acceptor A in a non-conjugated manner, structures of the bridge B1 and the bridge B2 are each independently selected from the group consisting of Formula IV and Formula V:

A1#,   Formula IV

A2—A3#,   Formula V where # represents a linking site of the bridge B1 and the bridge B2 for connecting to the electron donor D or the electron acceptor A;

A1 is selected from the group consisting of

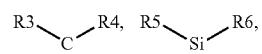

O, S and

A2 is selected from the group consisting of

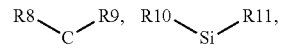

O, S,

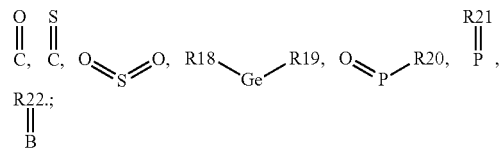

A3 is selected from the group consisting of

O, S

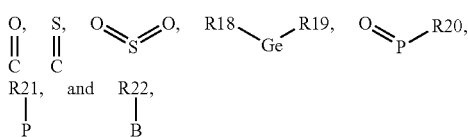

each of R3 to R17 is independently selected from the group consisting of —H, substituted or unsubstituted alkyl, cycloalkyl, substituted or unsubstituted alkenyl, substituted or unsubstituted alkynyl, substituted or unsubstituted aryl, substituted or unsubstituted heteroaryl, alkoxy (—OR'), thioalkyl (—SR'), sulfonyl (—SO₂R'), acyl (—COR'), formyl (—CHO), carboxyl (—CO₂R'), boryl (—BR'R"), sulfinyl (—SOR'), amine (—NR'R"), phosphino (—PR'R"), phosphinyl (—POR'R"), amido (—NR'COR"), silyl (—SiR'R"R'"), cyano (—CN), nitro (—NO₂), nitroso (—NO), isocyanato (—NCO), thiocyano (—NCS), and halogen, where R', R", and R'" each have the same definition as R3 to R17;

at least one of R8, R9, R13, and R14 is the substituted or unsubstituted alkyl, the cycloalkyl, the substituted or unsubstituted alkenyl, the substituted or unsubstituted alkynyl, the substituted or unsubstituted aryl, the substituted or unsubstituted heteroaryl, the alkoxy, the thioalkyl, the sulfonyl, the acyl, the formyl, the carboxyl, the boryl, the sulfinyl, the amine, the phosphino, the phosphinyl, the amido, the silyl, cyano (—CN), nitro (—NO₂), nitroso (—NO), isocyanato (—NCO), thiocyano (—NCS), or halogen;

each of R18 to R22 is independently selected from the group consisting of -H, substituted or unsubstituted alkyl, cycloalkyl, substituted or unsubstituted alkenyl, substituted or unsubstituted alkynyl, substituted or unsubstituted aryl, substituted or unsubstituted heteroaryl, alkoxy (—OR'), thioalkyl (—SR'), sulfonyl (—SO₂R'), acyl (—COR'), formyl (—CHO), carboxyl (—CO₂R'), boryl (—BR'R"), sulfinyl (—SOR'), amine (—NR'R"), phosphino (—PR'R"), phosphinyl (—POR'R"), amido (—NR'COR"), silyl (—SiR'R"R'"), cyano (—CN), nitro (—NO₂), nitroso (—NO), isocyanato (—NCO), thiocyano (—NCS), and halogen, where R', R", and R'" each have the same definition as R3;

the halogen is selected from the group consisting of —F, —Cl, —Br, and —I, the electron donor D and the electron acceptor A each independently include an aromatic or heteroaromatic group represented by Formula II or Formula III,

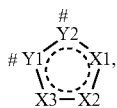

Formula II

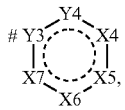

Formula III wherein the electron donor D and the electron acceptor A are different from each other, Formula II and Formula III are optionally part of a fused ring system, and Formula II and Formula III have # positions, the electron donor D and the electron acceptor A are linked to the bridge B1 and bridge B2 via the # positions, Y1, Y2, Y3, and Y4 are independently selected from the group consisting of C and N, each of X4 to X7 is independently selected from the group consisting of N, CH, NH, and C-R1 and at least one of X4 to X7 is C-R1, each of X1 to X3 is independently selected from the group consisting of N, O, S, Se, CH, NH, and C-R1, and at least one of X1 to X3 is C-R1, wherein R1 is independently selected from the group consisting of cycloalkyl, thioalkyl (—SR'), sulfonyl (—SO₂R'), acyl (—COR'), formyl (—CHO), carboxyl (—CO₂R'), boryl (—BR'R"), sulfinyl (—SOR'), amine (—NR'R"), phosphino (—PR'R"), phosphinyl (—POR'R"), amido (—NR'COR"), nitro (—NO₂), nitroso (—NO), isocyanato (—NCO), and thiocyano (—NCS), wherein R', R", and R'" each have the same definition as R1, and R', R", and R'" are optionally linked to each other to form an additional aliphatic, aromatic, or heteroaromatic ring system, and the cycloalkyl is selected from the group consisting of cyclopropyl, cyclopentyl, cyclohexyl, and the energy difference ΔE(S1-T1) between the lowest excited singlet (S1) state of the organic molecule and the triplet (T1) state of the organic molecule is less than 2000 cm⁻¹.

4. An organic molecule for luminescence, wherein the organic molecule is selected from the group consisting of compounds 13-21 and 25-64,

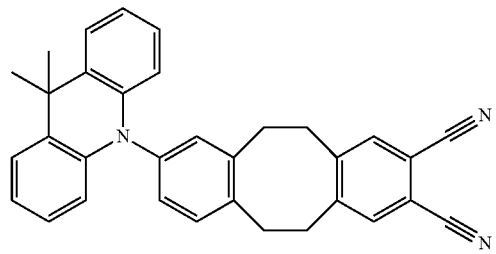

13

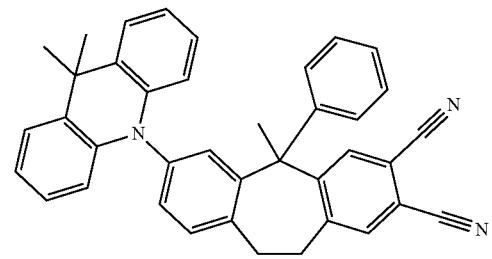

14

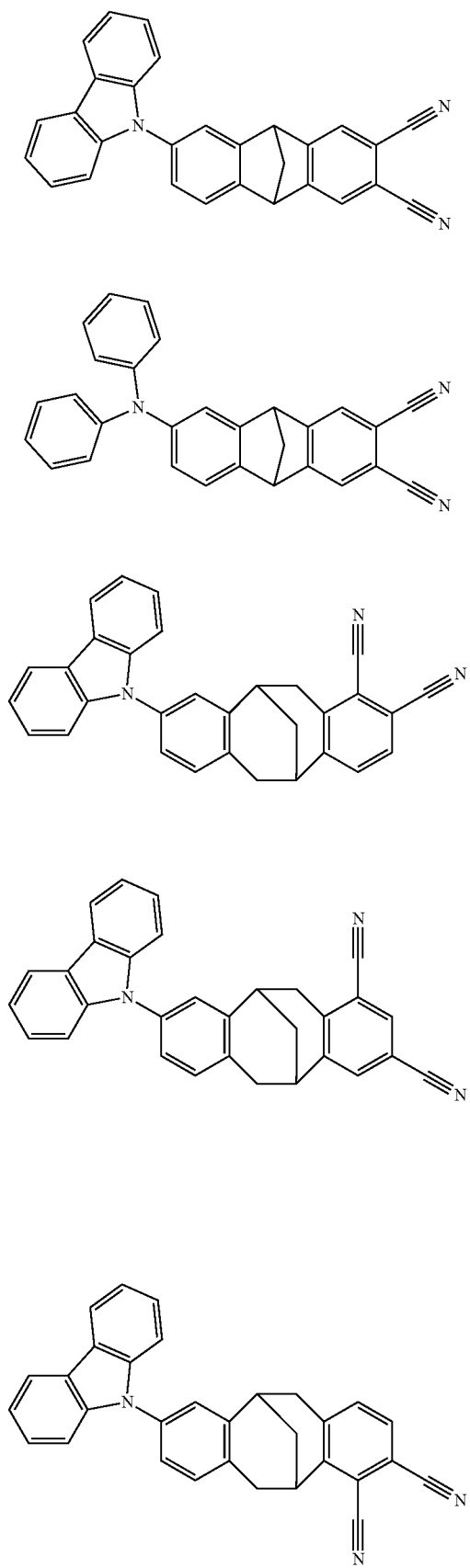
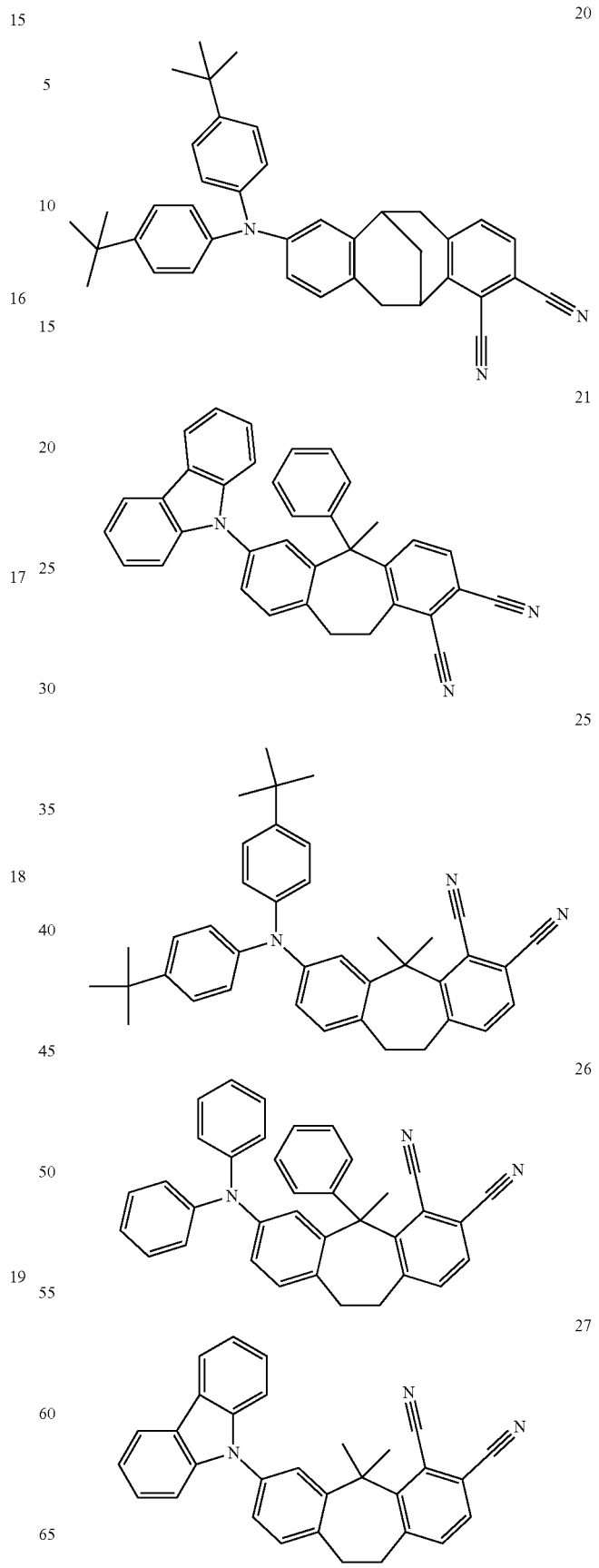

28
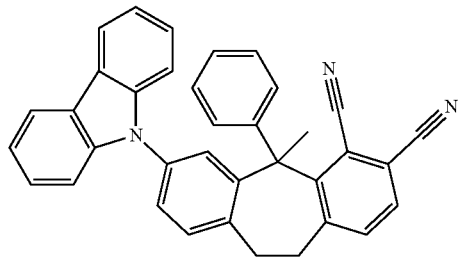
29
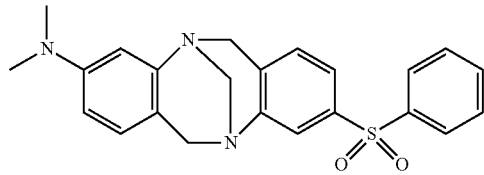
30
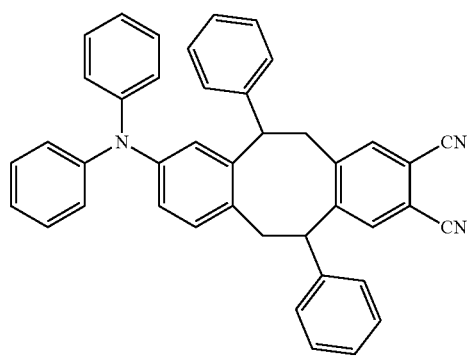
31
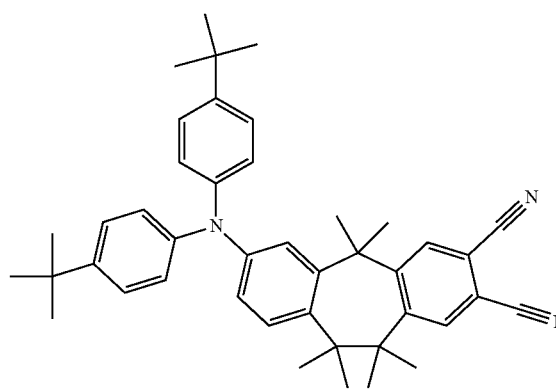
32
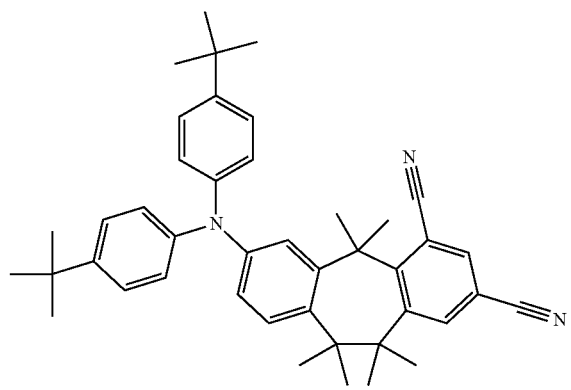
33
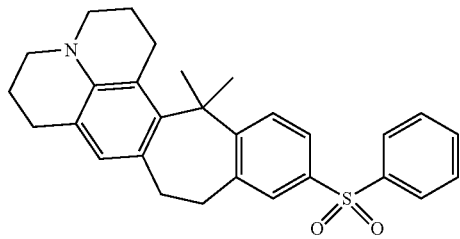
34
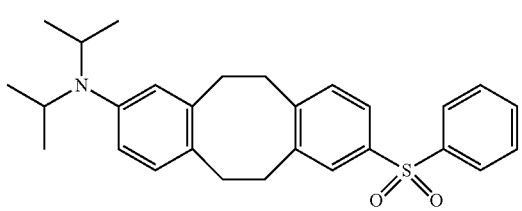
35
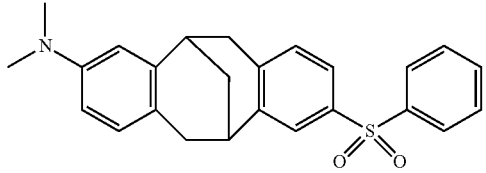
36
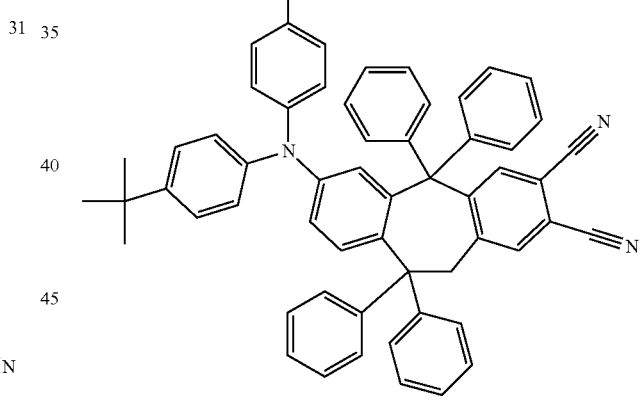
37
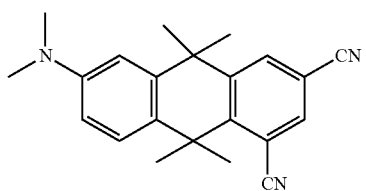
38
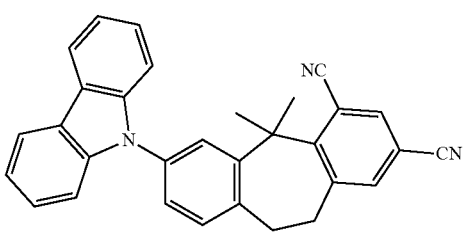

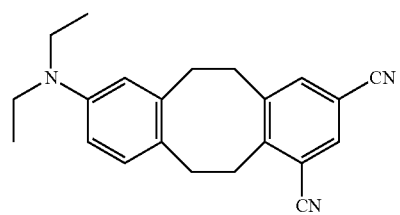
39
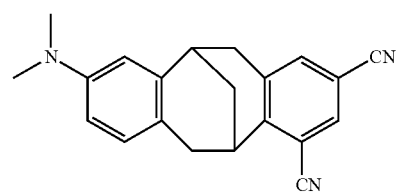
40
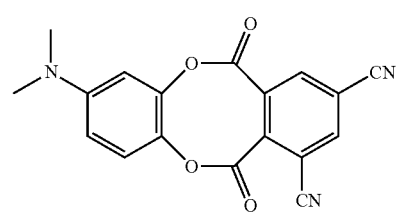
41
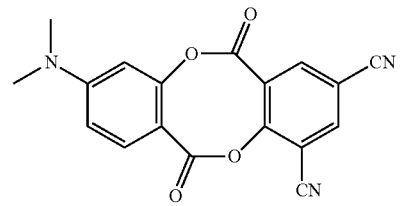
42
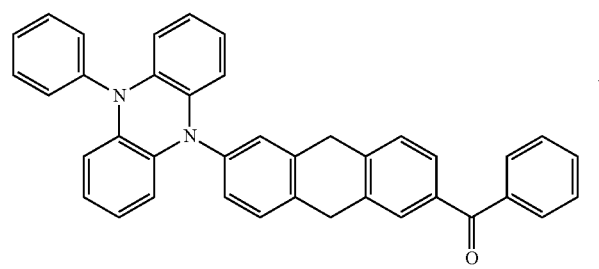
43
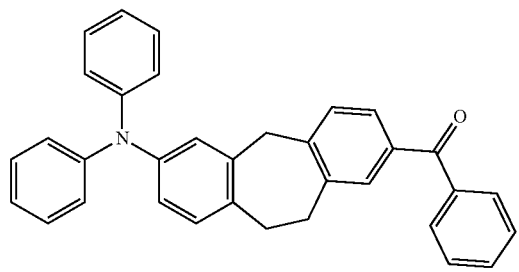
44
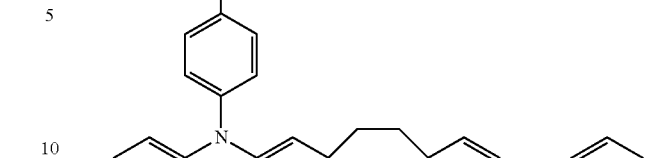
45
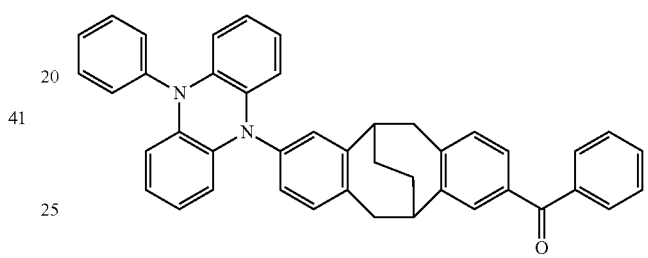
46
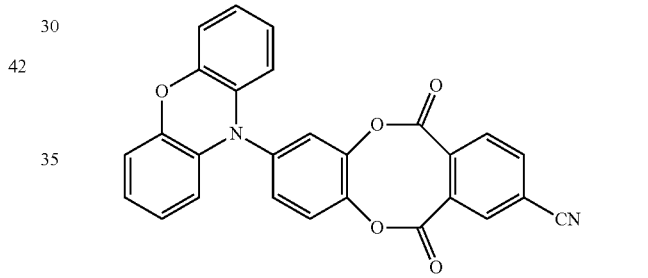
47
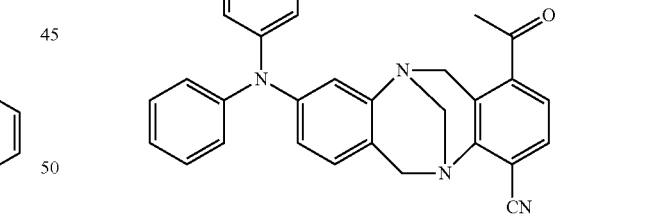
48
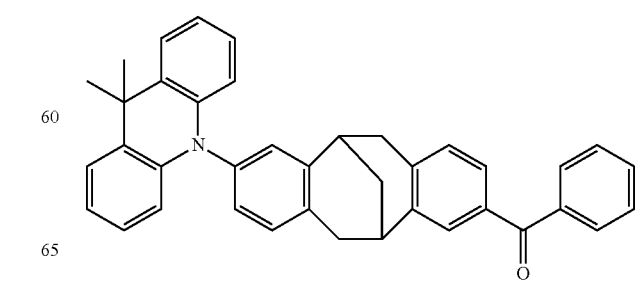
49

50
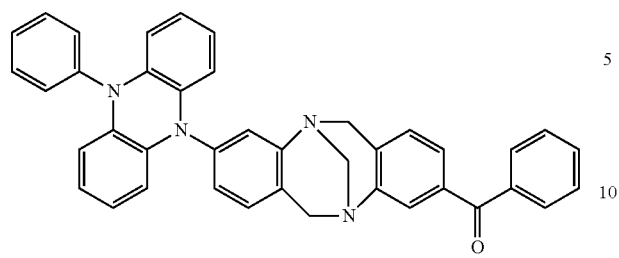
51
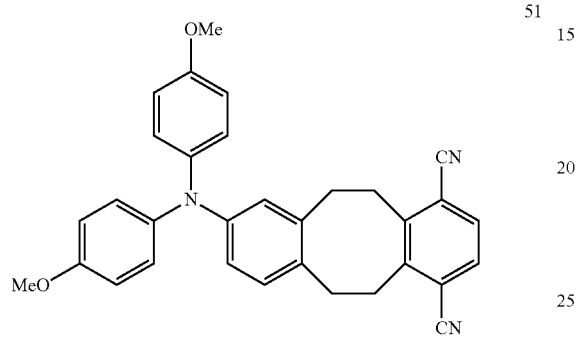
52
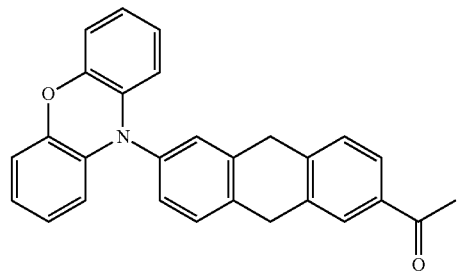
53
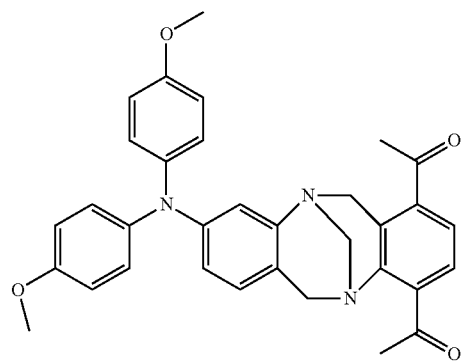
54
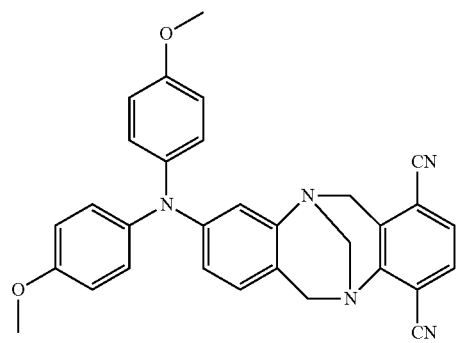
55
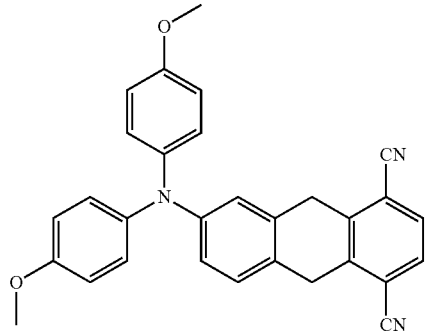
56
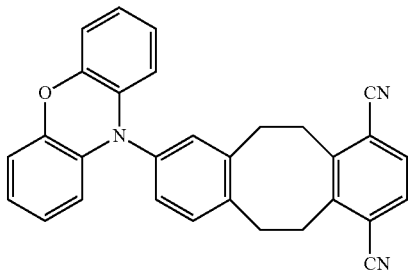
57
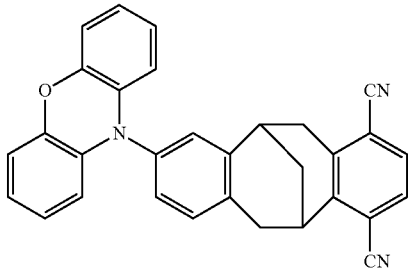
58
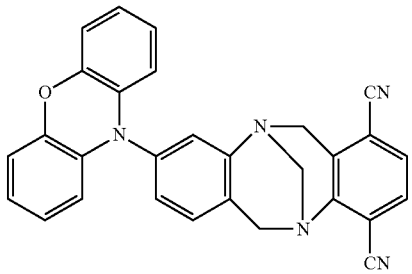
59
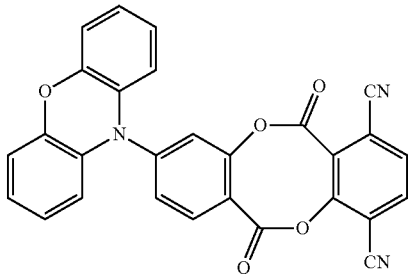

60
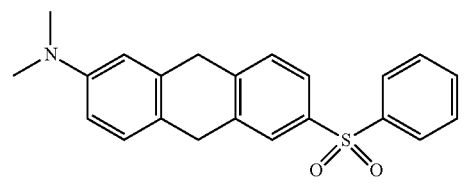
61
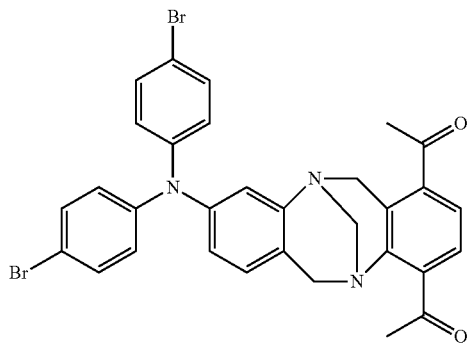
62
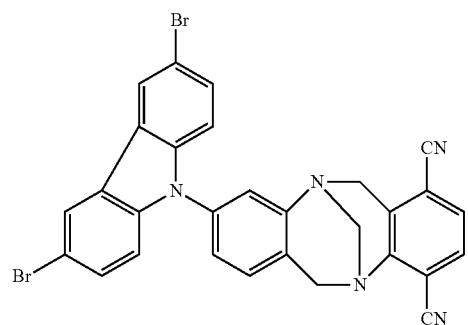
63
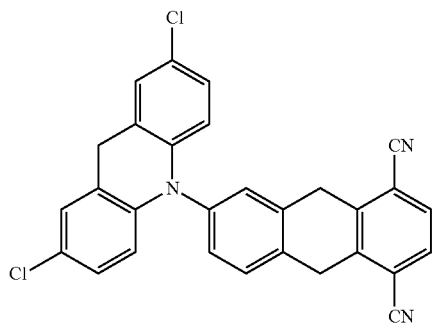
64
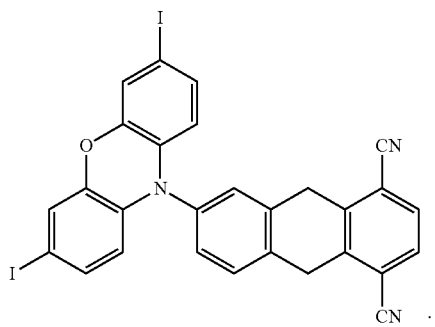
* * * * *